(12) United States Patent
Lee et al.

(10) Patent No.: US 9,439,986 B2
(45) Date of Patent: Sep. 13, 2016

(54) TRICARBONYL TECHNETIUM-99M, RHENIUM-185/187, OR RHENIUM-188 LABELED CYCLIC RGD DERIVATIVES AND USES THEREOF

(75) Inventors: Byung Chul Lee, Seoul (KR); Sang Eun Kim, Seoul (KR); Ji Sun Kim, Anyang-si (KR); Byung Seok Moon, Seoul (KR); Jae Ho Jung, Seoul (KR)

(73) Assignee: BIO IMAGING KOREA CO., LTD., Seoul (KR)

( * ) Notice: Subject to any disclaimer, the term of this patent is extended or adjusted under 35 U.S.C. 154(b) by 600 days.

(21) Appl. No.: 13/699,511

(22) PCT Filed: May 24, 2011

(86) PCT No.: PCT/KR2011/003801
§ 371 (c)(1),
(2), (4) Date: Nov. 21, 2012

(87) PCT Pub. No.: WO2011/149250
PCT Pub. Date: Dec. 1, 2011

(65) Prior Publication Data
US 2013/0064766 A1 Mar. 14, 2013

(30) Foreign Application Priority Data

May 24, 2010 (KR) .................. 10-2010-0048289
May 9, 2011 (KR) .................. 10-2011-0043544

(51) Int. Cl.
| | | |
|---|---|---|
| A61K 51/00 | (2006.01) | |
| A61M 36/14 | (2006.01) | |
| A61K 51/08 | (2006.01) | |
| C07K 7/64 | (2006.01) | |
| G01N 33/574 | (2006.01) | |
| G01N 33/60 | (2006.01) | |

(52) U.S. Cl.
CPC ........... *A61K 51/088* (2013.01); *A61K 51/082* (2013.01); *C07K 7/64* (2013.01); *G01N 33/574* (2013.01); *G01N 33/60* (2013.01)

(58) Field of Classification Search
CPC .............. A61K 38/00; A61K 38/085; A61K 38/1891; A61K 38/06; A61K 51/00; A61K 51/04; A61K 51/08; A61K 51/088; A61K 51/02; A61K 51/041; A61K 51/0474; A61K 51/082; A61K 2123/00; A61K 2121/00; C07K 7/00; C07K 7/14; C07K 7/50; C07K 7/64; C07K 5/00; C07K 5/08; G01N 33/60; G01N 33/574
USPC .............. 424/1.11, 1.65, 1.69, 9.1, 9.2, 9.4; 514/1, 1.1, 19.2, 19.3, 21.1, 21.9; 534/7, 10–14; 530/300, 316, 317, 331
See application file for complete search history.

(56) References Cited

U.S. PATENT DOCUMENTS

| | | | |
|---|---|---|---|
| 2007/0077195 A1* | 4/2007 | Alberto et al. | ............... 424/1.11 |
| 2008/0219921 A1 | 9/2008 | Bhalla | |
| 2015/0151011 A1* | 6/2015 | Jang et al. | .................... 424/1.11 |

FOREIGN PATENT DOCUMENTS

CN 101474415 A 7/2009

OTHER PUBLICATIONS

Lee et al, Bioorganic & Medicinal Chemistry, 2007, vol. 15, pp. 7755-7764.*
Byung Chul Lee, et al., Synthesis of Tc-99m labeled glucosamnio-Asp-cyclic(Arg-Gly-Asp-D-Phe-Lys) . . . , Bioorganic & Medicinal Chemistry. vol. 15, pp. 7755-7765, 2007.
Kyung-Ho Jung, et al., Favorable Biokinetic and Tumor-Targeting . . . , The Journal of Nuclear Medicine, vol. 47, No. 12, pp. 2000-2007, 2006.
Susana Alves, et al., In Vitro and In Vivo Evaluation of a Novel . . . , Bioconjugate Chem, vol. 18, pp. 530-537, 2007.
Roland Haubner, et al. Cancer Research, vol. 61, pp. 1781-1785, 2001.
Jae Min Jeong, et al., Preparation of a Promising Angiogenesis Pet Imaging . . . , The Journal of Nuclear Medicine, vol. 49, No. 5, pp. 830-836, 2008.
Xiaoyuan Chen, et al., MicroPET and Autoradiographic Imaging of Breast Cancer . . . , Bioconjugate Chem, vol. 15, pp. 41-49, 2004.
Shuang Liu, et al., Effect of Coligands on Biodistribution Characteristics . . . , Bioconjugate Chem., vol. 16, pp. 1580-1588, 2005.
Roland Haubner, et al., J. Nucl Med, vol. 40, pp. 1061-1071, 1999.
Marcel L. Janssen, et al., Tumor Targeting With Radiolabeled . . . , Cancer Research, vol. 62, pp. 6146-6151, 2002.
Yun Wu, PhD., et al., microPET Imaging of Glioma Integrin . . . , J. Nucl. Med, vol. 46, pp. 1707-1718, 2005.
Roger Alberto, et al., A Novel Organometallic Aqua Complex . . . , J. Am. Chem. Soc., vol. 120, pp. 7987-7988, 1998.
Roger Alberto, et al., First Application of . . . , J. Am. Chem. Soc., vol. 121, pp. 6076-6077, 1999.
R. Schibli, et al., First Organometallic Inhibitors for Human . . . , Journal of Organometallic Chem., vol. 668, pp. 67-74, 2003.
Roger Schibli, et al., Steps Toward High Specific Activity Labeling . . . , Bioconjugate Chem, vol. 13, pp. 750-756, 2002.

(Continued)

*Primary Examiner* — D L Jones
(74) *Attorney, Agent, or Firm* — Lucas & Mercanti, LLP

(57) ABSTRACT

The present invention relates to tricarbonyl technetium-99m or rhenium-188 labeled cyclic RGD derivatives, a preparation method thereof, and a pharmaceutical composition containing the derivative as an active ingredient for use in the diagnosis or treatment (radiotherapy) of angiogenesis-related diseases. The tricarbonyl technetium-99m or rhenium-188 labeled cyclic RGD derivatives of the present invention has a high subnanomolar affinity to integrin $\alpha_v\beta_3$ (also called as a vitronectin receptor) that is activated in an angiogenic action induced by a tumor, and acts exclusively upon cancer cells having selectively activated integrin $\alpha_v\beta_3$ because of a substantially low intake into the liver and intestines.

10 Claims, 8 Drawing Sheets

(56) References Cited

OTHER PUBLICATIONS

Guang-hui NI, et al; Advances in the study of the integrin . . . ; Acta Pharmaceutica Sinica; 2006; 41; 7; pp. 577-582.
Yun-peng Huang, et al; The role of integrin . . . ; Bulletin of Chinese Cancer; 2007; 16; 1; pp. 35-38.
P. Bouziotis, et al; Radiolabeled biomolecules for early cancer detection and therapy via angiogenesis targeting; ScienceDirect; Nuclear Instruments and Methods in Physics Research A; 569; 2006; pp. 492-496.
Dong-Eun Lee, et al; Preparation and evaluation of 99m TC-labeled cyclic . . . ; Applied Radiation and Isotopes; 68; 2010; pp. 1896-1902.

* cited by examiner

Tumor

TRICARBONYL TECHNETIUM-99M, RHENIUM-185/187, OR RHENIUM-188 LABELED CYCLIC RGD DERIVATIVES AND USES THEREOF

CROSS-REFERENCE TO RELATED APPLICATIONS

This patent application is a U.S. national phase entry, under 35 U.S.C. §371, of PCT/KR2011/003801 filed on May 24, 2011, which claims the benefit of priority from Korean Patent Application Nos. 10-2010-0048289 and 10-2011-0043544, filed on May 24, 2010 and May 9, 2011, respectively, the contents of each of which are incorporated herein by reference in its entirety.

BACKGROUND OF THE INVENTION

1. Field of the Invention

The present invention relates to tricarbonyl technetium-99m or rhenium-188 labeled cyclic RGD derivatives, a preparation method thereof, and a pharmaceutical composition containing the derivatives as an active ingredient for use in the diagnosis or treatment of angiogenesis-related disease.

2. Description of the Related Art

The nuclear medicine diagnosis and treatment technologies, which are capable of noninvasive technique for a disease at molecular level using radiotracers with specificity to target molecules, is considered important more than ever because the current medicinal field has a main goal of complete cancer treatment.

The positron emission tomography (PET) is generally used for the diagnosis of cancer in vivo, using radiopharmaceutical such as [$^{18}$F]-FDG(2-fluoro-deoxy-D-glucose). However, [$^{18}$F]-FDG is not possible to diagnose of brain tumor, or distinguish between inflammation and tumor, and also has a limitation that it cannot provide information about angiogenesis and symptoms of metastasis.

Angiogenesis is indispensable in the primary or metastatic tumor. Tumor tissues do not grow more than 1-2 mm$^3$ without supply of nutrients and oxygen from the new vessels. That is, angiogenesis leads to formation of metastatic cancer at other sites through blood vessels during neovascularization. Accordingly, imaging for targeting of new vessels has a potential to be applied commonly for most of solid tumor. In terms of treatment, the conventional chemotherapy focuses on the rapid growth of cancer cells, and thus displays toxicity to normal cells including bone marrow cells and gastrointestinal cells. Compared to the above, a treatment (radiotherapy) targeting angiogenesis brings in relatively less side-effect associated with prolonged administration, and less risk of developing a tolerance because the treatment focuses on vascular cells.

As well known, the growth mechanism of cancer begins as vessels near the cancer tissues have over of $\alpha_v\beta_3$ integrin. Integrin is heterodimer membrane protein consisting of $\alpha$ and $\beta$ submits involved with adhesion or transport of the cells. Among various types of integrins, integrin $\alpha_v\beta_3$, also called vitronectin receptor, is considered important in the angiogenesis. This particular integrin does not express in normal vascular endothelial cells, because the integrin expresses only when tumor-triggered angiogenesis is activated. The Arg-Gly-Asp (RGD) peptide sequence is commonly known for binding with this integrin. Based on this sequence, cyclic Arg-Gly-Asp (cRGD) peptide compound is reported to be an antagonist having higher binding affinity to block normal function of integrin $\alpha_v\beta_3$, and many research groups have been carried out for imaging of cancer angiogenesis worldwide, by introducing a variety of radioisotopes in this particular compound.

Radioisotopes such as fluorine-18, gallium-68 and copper-64 for PET, and technetium-99m, iodine-123, and indium-111 for SPECT have been used in various cyclic RGD derivatives, added with monosaccharide to enhance pharmacokinetics of the radiotracer, or added with dimeric or tetrameric cyclic RGD to further enhance binding affinity (Haubner, R., Wester, H.-J., Weber, W. A., Mang, C., Ziegler, S. I., Goodman, S. L., Senekowi tsch-Schmidtke, R., Kessler, H., Schwa iger, M. Cancer Res., 2001, 61:1781-1785; Jeong, J. M., Hong, M. K., Chang, Y. S., Lee Y. S., Kim, Y. J., Cheon, G. J., Lee, D. S., Chung, J. K., Lee, M., J. Nucl Med., 2008, 49:830-836; Chen, W., Park, R., Tohme, M., Shahinian, A. H. Bading, J. R., Cont i, P. S. Bioconjugate Chem., 2004, 15:41-49; Liu, S., Hsieh W. Y., Kim, Y. S., Mohammel, S. I., Bioconjugate Chem., 2005, 16:1580-1588 Haubner, R., Wester, H-J., Reuning, U., Senekowitsch_Schmidtke, R. Diefenbach, B., Kessler, H., Stocklin G., Schwa iger, M., J. Nucl. Med., 1999 40:1061-1071; Jansen, M., Oyen, W. J. G., Dijkgraaf, I., Massuger, L. F. A. G. Friel ink, C., Edwards, D. S., Rajo adyhe, M., Boonstra, H., Corsten, F. H. M. Boerman, O., Cancer Res., 2002, 62:6146-6151; Wu, Y., Zhang, X., Xiong, Z. Cheng, Z., Fisher, D. R., Liu, S., Gambhir, S. S., Chen, X., J. Nucl. Med. 2005, 46: 1707-1718). Despite the various radioisotope labeled cyclic RGD derivatives developed so far, the shortcomings such as high accumulation in liver and slow excretion from large intestines still keep as a radiotracer for diagnosis with limited efficiency due to low accumulation ratio between tumor and normal tissues. Further, clinical researches have not been made actively yet, especially, in case of radiotherapy, because the therapeutic radioisotope labeled radiotracers can effects on not only tumor but also normal tissues in the radiotherapy.

Among various radioisotopes, technetium-99m and rhenium-188 are considered outstanding in practical aspect, because diagnoses is enabled through single photon emission computed tomography (SPECT) simple labeling method and separating processes, while requiring only a generator. Further, it is possible to selectively label rhenium-188 using the same precursor for the purpose of radiotherapy.

However, the conventional method of labeling technetium-99m and rhenium-188 has shortcomings such as large pocket size to label of technetium-99m or rhenium-188, low in vivo stability, and difficult precursor synthesis, which in turn limit development of efficient radiotracers in many ways. Meanwhile, tricarbonyl technetium-99m and tricarbonyl rhenium-188 are acceptable for as the efficient radiotracers considering characteristics such as easy precursor synthesis, and small and metabolic stable labeling pocket, and it is also possible to change the charge of radiotracer in the preparation process sith a simple change.

Furthermore, these radiotracers have a good in vivo stability and rapid clearance without being accumulated at the thyroid at a metabolism, enabling relatively better imaging result. Use of tricarbonyl technetium-99m or tricarbonyl rhenium-188 is not extensively known, but under continuous researches worldwide for the development of new radiopharmaceuticals.

Accordingly, the present inventors synthesize novel tricarbonyl technetium-99m or rhenium-188 labeled cyclic RGD derivatives for targeting integrin $\alpha_v\beta_3$, a prime biomarker, for imaging and radiotherapy of cancer angiogenesis, and completed the present invention after confirming through various biological evaluations that the tricarbonyl technetium-99m or rhenium-188 labeled RGD derivatives are capable of diagnosing and treating various diseases related with angiogenesis.

SUMMARY OF THE INVENTION

An object of the present invention is to provide a tricarbonyl technetium-99m or rhenium-188 labeled cyclic RGD derivatives for advantageous use in the diagnosis or treatment of angiogenesis-related disease, or a pharmaceutically-acceptable salt thereof.

Another object of the present invention is to provide a preparation method of tricarbonyl technetium-99m or rhenium-188 labeled cyclic RGD derivatives.

Yet another object of the present invention is to provide precursors of a tricarbonyl technetium-99m or rhenium-188 labeled cyclic RGD derivatives.

Yet another object of the present invention is to provide a pharmaceutical composition containing the tricarbonyl technetium-99m or rhenium-188 labeled cyclic RGD derivatives or pharmaceutically-acceptable salt thereof as an active ingredient, for the diagnosis or treatment of angiogenesis-related disease.

In other to achieve the objects mentioned above, the present invention provides tricarbonyl technetium-99m or rhenium-188 labeled cyclic RGD derivatives of Formula 1 or a pharmaceutically-acceptable salt thereof.

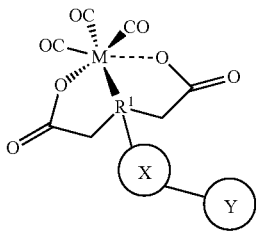

[Chemical Formula 1]

where, M, $R^1$, X and Y are as defined in the description.

Further, the present invention provides a preparation method of tricarbonyl technetium-99m or rhenium-188 labeled cyclic RGD derivatives.

Further, the present invention provides precursors of the tricarbonyl technetium-99m or rhenium-188 labeled cyclic RGD derivative.

Further, the present invention provides a pharmaceutical composition containing the tricarbonyl technetium-99m or rhenium-188 labeled cyclic RGD derivatives or pharmaceutically-acceptable salt thereof as an active ingredient, for the diagnosis or treatment of angiogenesis-related disease.

The tricarbonyl technetium-99m or rhenium-188 labeled cyclic RGD derivative according to the present invention has a high affinity with subnanomolar level to integrin $\alpha_v\beta_3$, which is often called vitronectin receptor, activated in tumor-induced angiogenesis, reflects high resolution tumor imaging in tumor cell-transplanted animal model after initial intake of tricarbonyl technetium-99m labeled cyclic RGD derivative, markedly reduced intake in liver and large intestines compared to the conventionally-known radioisotope labeled cyclic RGD derivatives and thus is effective only on the positive integrin $\alpha_v\beta_3$ cancer cells. Based on the above findings, it was confirmed that the rhenium-188 labeled derivative using the same precursor as that used for technetium-99m displayed effective growth inhibitory effect and treatment efficacy when intravenously injected to tail vein of tumor animal model, compared to a tumor animal model injected with only saline solution, and thus can be advantageously used as a pharmaceutical customized for the diagnosis or treatment of angiogenesis-related disease.

BRIEF DESCRIPTION OF THE DRAWINGS

The foregoing and/or other aspects of the present invention will be more apparent upon reading the description of certain exemplary embodiments with reference to the accompanying drawings, in which.

DETAILED DESCRIPTION OF THE INVENTION

Figure 1:
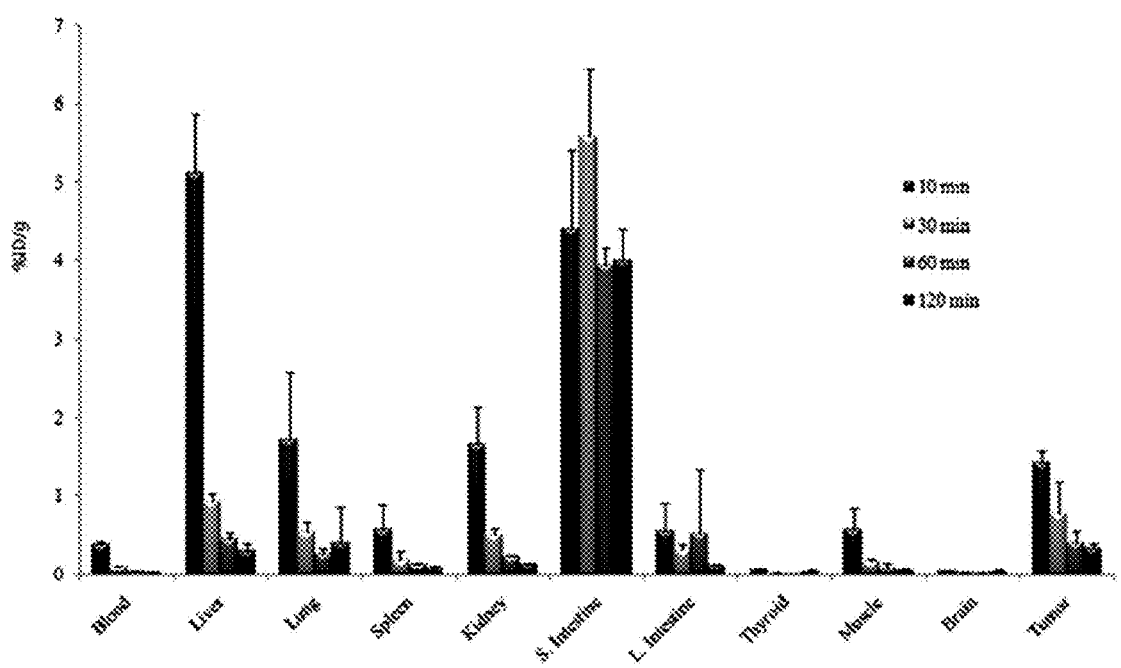
FIG. 1 is a graph showing the result of measuring uptake and excretion rates of tricarbonyl technetium-99m labeled cyclic RGD derivative according to an embodiment of the present invention in/from in vivo tumor model mice.

Hereinafter, the present invention will be explained in detail.

The present invention provides tricarbonyl technetium-99m or rhenium labeled cyclic RGD derivatives expressed by Chemical Formula 1 or a pharmaceutically acceptable salt thereof:

[Chemical Formula 1]

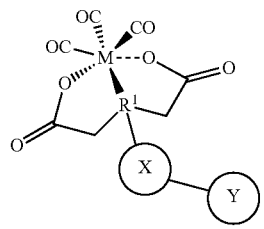

where, M is $^{99m}$Tc, $^{188}$Re or $^{185/187}$Re,

R1 is N, $N(CH_2CH_2O)_nCH_2CH_2CONH$ or $N(CH_2CONH)_4CH_2CH_2CONH$,

X is direct bond,

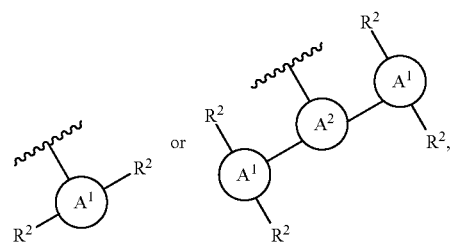

$A^1$ and $A^2$ are each amino acid selected from a group consisting of aspartic acid, lysine, glutamic acid, tyrosine, cysteine, threonine and serine, $R^2$ is NH or $NH(Z)_nCH_2CH_2CONH$, Z is —$CH_2CH_2O$— or —$CH_2CONH$—, n is an integer between 0 and 8, Y is

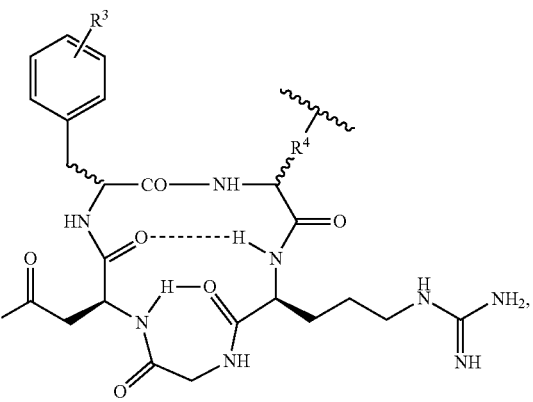

$R^3$ is H or OH, $R^4$ is —$(CH_2)_m$— or —$(CH_2)_m$—COO—, m is an integer between 1 and 8, and Y is directed bound to 1 or bound to $R^2$ among X.

The tricarbonyl technetium-99m or rhenium labeled cyclic RGD derivatives according to the present invention may preferably be selected from a group of compounds represented by:

[Chemical Formula 1A]

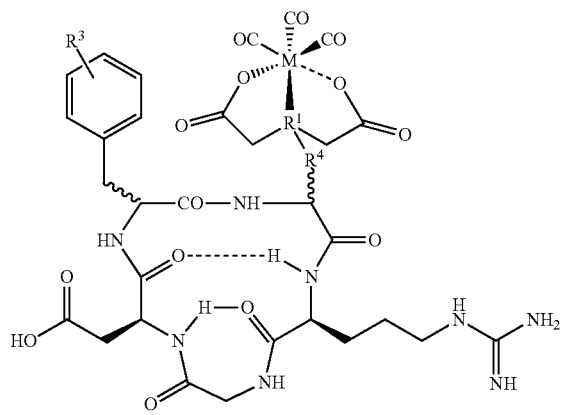

-continued
[Chemical Formula 1B]
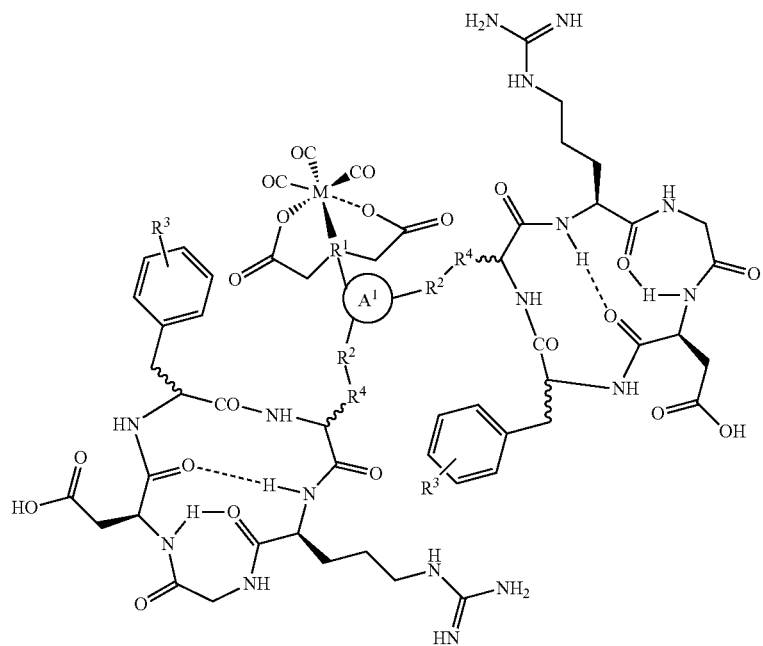
[Chemical Formula 1C]
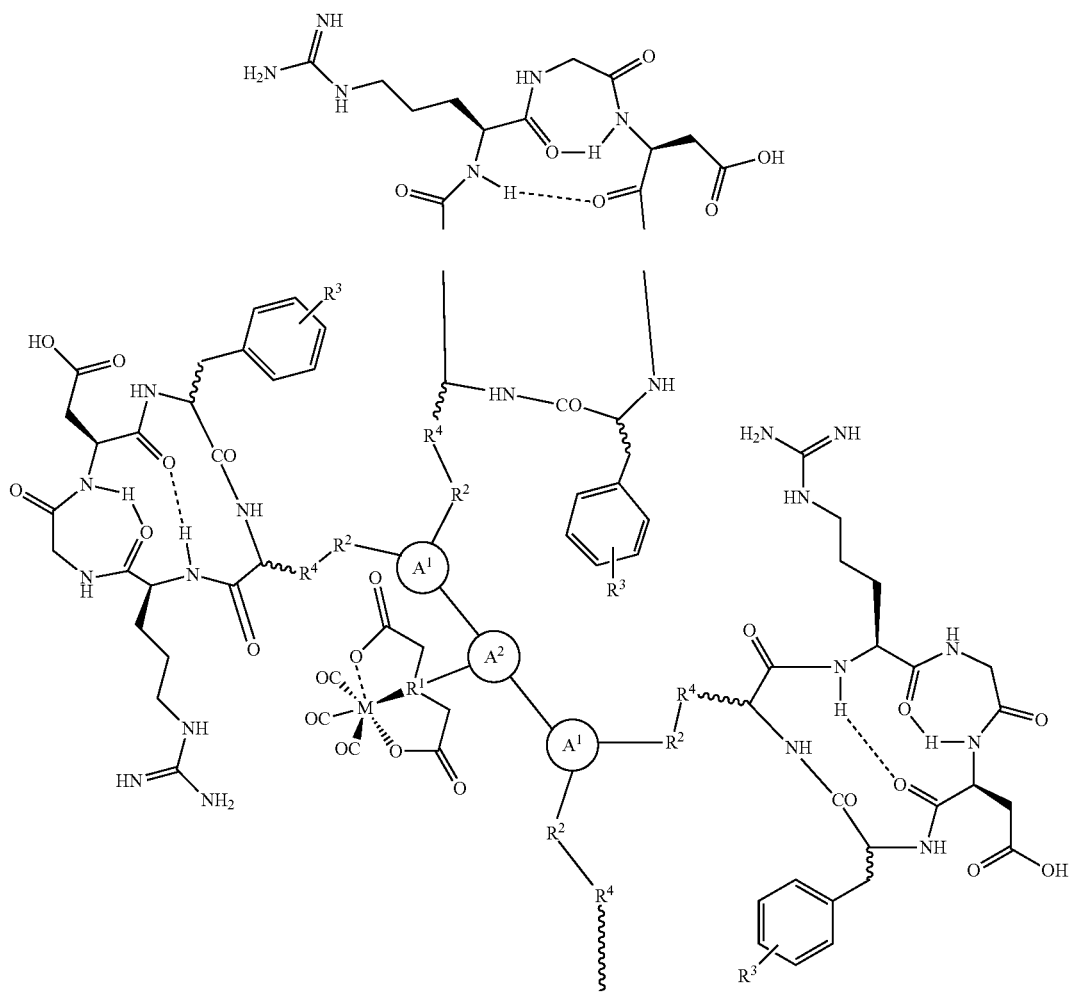

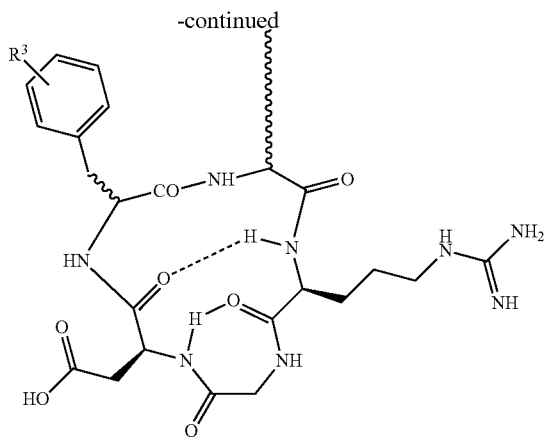

where, M, $R^1$, $R^2$, $R^3$, $R^4$, $A^1$ and $A^2$ are as defined in Chemical Formula 1.

The tricarbonyl technetium-99m or rhenium labeled cyclic derivatives expressed by Chemical Formula 1 according to a preferred embodiment of the present invention is as follows.

The tricarbonyl technetium-99m or rhenium-188 labeled cyclic derivative expressed by Chemical Formula 1 according to a preferred embodiment of the present invention is as follows.

1) cyclic {(tricarbonyl-[$^{99m}$Tc]technetium-N-α-bis-hydroxycarbonyl methyl-lysine)-alginine-glycine-aspartic acid-D-phenylalanine};
2) cyclic {(tricarbonyl-[$^{188}$Re]rhenium-N-α-bis-hydroxycarbonyl methyl-lysine)-alginine-glycine-aspartic acid-D-phenylalanine};
3) cyclic {(tricarbonyl-[$^{185/187}$Re]rhenium-N-α-bis-hydroxycarbonyl methyl-lysine)-alginine-glycine-aspartic acid-D-phenylalanine};
4) cyclic {(tricarbonyl-[$^{99m}$Tc]technetium-N-α-bis-hydroxycarbonyl methyl-$NH_2(CH_2CH_2O)_4CH_2CH_2$ CONH-lysine)-alginine-glycine-aspartic acid-D-phenylalanine};
5) cyclic {(tricarbonyl-[$^{188}$Re]rhenium-N-α-bis-hydroxycarbonyl methyl-$NH_2(CH_2CH_2O)_4CH_2CH_2CONH$-lysine)-alginine-glycine-aspartic acid-D-phenylalanine};
6) cyclic {(tricarbonyl-[$^{185/187}$Re]rhenium-N-α-bis-hydroxycarbonyl methyl-$NH_2(CH_2CH_2O)_4CH_2CH_2$ CONH-lysine)-alginine-glycine-aspartic acid-D-phenylalanine};
7) cyclic {(tricarbonyl-[$^{99m}$Tc]technetium-N-α-bis-hydroxycarbonyl methyl-glycine-$CONH(CH_2CH_2O)_4CH_2$ $CH_2CONH$-lysine)-alginine-glycine-aspartic acid-phenylalanine};
8) cyclic {(tricarbonyl-[$^{188}$Re]rhenium-N-α-bis-hydroxycarbonyl methyl-glycine-$CONH(CH_2CH_2O)_4CH_2CH_2$ CONH-lysine)-alginine-glycine-aspartic acid-D-phenylalanine};
9) cyclic {(tricarbonyl-[$^{185/187}$Re]rhenium-N-α-bis-hydroxycarbonyl methyl-glycine-$CONH(CH_2CH_2O)_4CH_2$ $CH_2CONH$-lysine)-alginine-glycine-aspartic acid-D-phenylalanine};
10) (tricarbonyl-[$^{99m}$Tc]technetium-N-α-bis-hydroxycarbonyl methyl-aspartic acid)-[cyclic (lysine-alginine-glycine-aspartic acid-D-phenylalanine)]$_2$;
11) (tricarbonyl-[$^{188}$Re]rhenium-N-α-bis-hydroxycarbonyl methyl-aspartic acid)-[cyclic (lysine-alginine-glycine-aspartic acid-D-phenylalanine)]$_2$;
12) (tricarbonyl-[$^{185/187}$Re]rhenium-N-α-bis-hydroxycarbonyl methyl-aspartic acid)-[cyclic (lysine-alginine-glycine-aspartic acid-D-phenylalanine)]$_2$;
13) {tricarbonyl-[$^{99m}$Tc]technetium-N-α-bis-hydroxycarbonyl methyl-(polyethylene glycol)$_n$-aspartic acid}-[cyclic (lysine-alginine-glycine-aspartic acid-D-phenylalanine)]$_2$, (n=0-8);
14) {tricarbonyl-[$^{188}$Re]rhenium-N-α-bis-hydroxycarbonyl methyl-(polyethylene glycol)$_n$-aspartic acid}-[cyclic (lysine-alginine-glycine-aspartic acid-D-phenylalanine)]$_2$, (n=0-8);
15) {tricarbonyl-[$^{185/187}$Re]rhenium-N-α-bis-hydroxycarbonyl methyl-(polyethylene glycol)$_n$-aspartic acid}-[cyclic (lysine-alginine-glycine-aspartic acid-D-phenylalanine)]$_2$, (n=0-8);
16) {tricarbonyl-[$^{99m}$Tc]technetium-N-α-bis-hydroxycarbonyl methyl-(polyethylene glycol)$_n$-aspartic acid}-{(polyethylene glycol)$_n$-[cyclic (lysine-alginine-glycine-aspartic acid-D-phenylalanine)]}$_2$, (n=0-8);
17) {tricarbonyl-[$^{188}$Re]rhenium-N-α-bis-hydroxycarbonyl methyl-(polyethylene glycol)$_n$-aspartic acid}-{(polyethylene glycol)$_n$-[cyclic (lysine-alginine-glycine-aspartic acid-D-phenylalanine)]}$_2$, (n=0-8);
18) {tricarbonyl-[$^{185/187}$Re]rhenium-N-α-bis-hydroxycarbonyl methyl-(polyethylene glycol)$_n$-aspartic acid}-{(polyethylene glycol)$_n$-[cyclic (lysine-alginine-glycine-aspartic acid-D-phenylalanine)]}$_2$, (n=0-8);
19) (tricarbonyl-[$^{99m}$Tc]technetium-N-α-bis-hydroxycarbonyl methyl-aspartic acid)-{aspartic acid-[cyclic (lysine-alginine-glycine-aspartic acid-D-phenylalanine)]$_2$}$_4$;
20) (tricarbonyl-[$^{188}$Re]rhenium-N-α-bis-hydroxycarbonyl methyl-aspartic acid)-{aspartic acid-[cyclic (lysine-alginine-glycine-aspartic acid-D-phenylalanine)]$_2$}
21) (tricarbonyl-[$^{185/187}$Re]rhenium-N-α-bis-hydroxycarbonyl methyl-aspartic acid)-{aspartic acid-[cyclic (lysine-alginine-glycine-aspartic acid-D-phenylalanine)]$_2$}$_4$;
22) {tricarbonyl-[$^{99m}$Tc]technetium-N-α-bis-hydroxycarbonyl methyl-(polyethylene glycol)$_n$-aspartic acid}-{aspartic acid-[cyclic (lysine-alginine-glycine-aspartic acid-D-phenylalanine)]$_2$}$_4$, (n=0-8);
23) {tricarbonyl-[$^{188}$Re]rhenium-N-α-bis-hydroxycarbonyl methyl-(polyethylene glycol)$_n$-aspartic acid}-{aspartic acid-[cyclic (lysine-alginine-glycine-aspartic acid-D-phenylalanine)]$_2$}$_4$, (n=0-8);
24) {tricarbonyl-[$^{185/187}$Re]rhenium-N-α-bis-hydroxycarbonyl methyl-(polyethylene glycol)$_n$-aspartic acid}-{aspartic acid-[cyclic (lysine-alginine-glycine-aspartic acid-D-phenylalanine)]$_2$}$_4$, (n=0-8);

25) {tricarbonyl-[$^{99m}$Tc]technetium-N-α-bis-hydroxycarbonyl methyl-(polyethylene glycol)$_n$-aspartic acid}-{aspartic acid-(polyethylene glycol)$_n$-[cyclic (lysine-alginine-glycine-aspartic acid-D-phenylalanine)]$_2$}$_4$, (n=0-8);

26) {tricarbonyl-[$^{188}$Re]rhenium-N-α-bis-hydroxycarbonyl methyl-(polyethylene glycol)$_n$-aspartic acid}-{aspartic acid-(polyethylene glycol)$_n$-[cyclic (lysine-alginine-glycine-aspartic acid-D-phenylalanine)]$_2$}$_4$, (n=0-8); and 27) {tricarbonyl-[$^{185/187}$Re]rhenium-N-α-bis-hydroxycarbonyl methyl-(polyethylene glycol)$_n$-aspartic acid}-{aspartic acid-(polyethylene glycol)$_n$-[cyclic (lysine-alginine-glycine-aspartic acid-D-phenylalanine)]$_2$}$_4$, (n=0-8).

The cyclic RGD derivative of Chemical Formula 1 according to the present invention may include one to four RGD rings.

The cyclic RGD derivative expressed by Chemical Formula 1 according to the present invention may be available in the form of pharmaceutically acceptable salt. The pharmaceutically acceptable salt may advantageously be an acid-addition salt formed by pharmaceutically or biologically acceptable various organic or inorganic acids. The appropriate organic acid may include, for example, carboxylic acid, phosphoric acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenyl acetic acid, benzene sulfonic acid, 2-naphthalene sulfonic acid, methyl sulfate, ethyl sulfate, or dodecyl sulfate, and appropriate inorganic acid may include, for example, hydrochloric acid, sulfuric acid or phosphoric acid.

The cyclic RGD derivative expressed by Chemical Formula 1 according to the present invention may include not only the pharmaceutically acceptable salt, but also any salt, hydrate and solvate that can be prepared by the known method.

Further, the present invention provides a method for preparing cyclic RGD derivative of Chemical Formula 1.

To be specific, the cyclic RGD derivative according to the present invention may be prepared by the method as represented by Reaction Formulae 1 and 2.

Preparative Method 1

According to the present invention, as represented by Reaction Formula 1, the cyclic RGD derivative labeled with radioisotope, i.e., tricarbonyl technetium-99m or tricarbonyl rhenium-188 by a method comprising a step of reacting tricarbonyl moiety with technetium-99m or rhenium-188 using a precursor compound of Formula 2 to prepare a cyclic RGD derivative labeled with the tricarbonyl technetium-99m or tricarbonyl rhenium-188 of Formula 1.

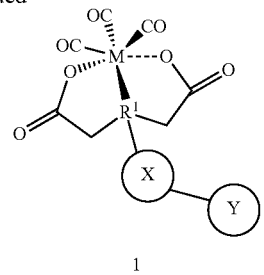

Where, M is $^{99m}$Tc or $^{188}$Re, R$^1$, X and Y are as defined by Chemical Formula 1.

To be specific, cyclic RGD derivative labeled with tricarbonyl technetium-99m or tricarbonyl rhenium-188 may be prepared by diluting the tricarbonyl technetium-99m or tricarbonyl rhenium-188 compound ($^{99m}$Tc(CO)$_3$(H$_2$O)$_3$$^+$ or $^{188}$Re(CO)$_3$(H$_2$O)$_3$$^+$) in 0.5~5 mL of distilled water solvent, putting the same in a reaction container with precursor of Chemical Formula 2 therein, and allowing the content to react by heating at 70~80° C. for 30 minutes for technetium-99m labeling or 60 minutes for rhenium-188 labeling.

Regarding Preparative method 1 according to the present invention, the tricarbonyl technetium-99m or tricarbonyl rhenium-188 compound may be synthesized by the known method, or preferably by the methods documented as follows:

References: Alberto, R., Schibli, R., Egli, A., Schubiger, A. P., Abram, U., aden, T. A., J. Am. Chem. Soc. 1998, 120:7987-7988; Alberto, R., Schibli, R., Schubiger, A. P., Abram, U., Pietzsch, H-P., Johannsen, B., J. Am. Chem. Soc. 1999, 121:6076-6077; Schibli, R., Netter, M., Scapozza, L., Birringer, M., Schel 1 ing, P., Dumas, C., Schoch, J., Schubiger, P. A., J. Organomet. Chem. 2003, 668:67-74; Schibli, R., Schwarzbach, R., Alberto, R., Ortner, K., Schmal le, H., Dumas, C., Egli, A., Schubiger, P. A. Bioconjuate Chem. 2002, 13:750-756.

The prepared cyclic RGD derivative labeled with tricarbonyl technetium-99m or tricarbonyl rhenium-188 may additionally be cooled at room temperature and isolated/purified by tC18 Sep-Pak cartridge or high performance liquid chromatography (HPLC).

Preparative Method 2

In one embodiment of the present invention, the cyclic RGD derivative introduced with the nonradioactive isotope, i.e., tricarbonyl $^{185/187}$Re may be prepared by a method comprising a step of putting (NEt$_4$)$_2$Re(CO)$_3$Br$_3$ to the precursor of Chemical Formula 2 and allowing the content to react to form the cyclic RGD derivative introduced with tricarbonyl $^{185/187}$Re of Chemical Formula 1a, as represented by the following reaction formula:

[Reaction Formula 1]

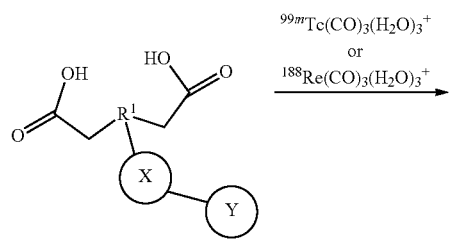

[Reaction Formula 2]

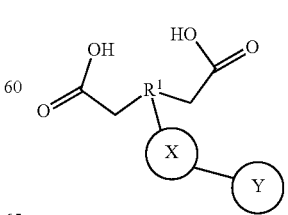

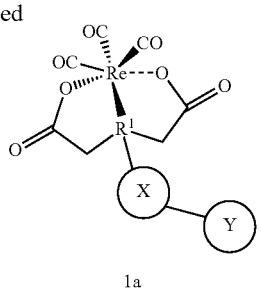

1a

Where, $R^1$, X and Y are as defined in Chemical Formula 1, and Chemical Formula 1a is included in Chemical Formula 1.

To be specific, the cyclic RGD derivative introduced with tricarbonyl $^{185/187}$Re of Chemical Formula 1a may be prepared by diluting the reagent $(NEt_4)_2Re(CO)_3Br_3$ in 0.5-5 mL of distilled water solvent, putting the result in a reaction container with precursor of Chemical Formula 2 therein, and allowing the content to react by heating at 70-80° C. for 55-65 minutes.

The cyclic RGD derivative introduced with tricarbonyl $^{185/187}$Re of Chemical Formula 1a is a standard compound of the cyclic RGD derivative labeled with tricarbonyl technetium-99m or tricarbonyl rhenium-188 of Reaction Formula 1, and is identical to the cyclic RGD derivative labeled with tricarbonyl rhenium-188, and thus has the same retention time in the HPLC, with a difference of about 1-2 minutes from the cyclic RGD derivative labeled with tricarbonyl technetium-99m.

The cyclic RGD derivative introduced with the prepared $^{185/187}$Re may additionally be cooled at room temperature and separated/purified by tC18 Sep-Pak cartridge or high performance liquid chromatography (HPLC).

Furthermore, the present invention provides a pharmaceutical composition for the diagnosis or treatment (radiotherapy) of angiogenesis-related diseases, comprising tricarbonyl technetium-99m or rhenium-188 labeled cyclic RGD derivative of Formula 1 or pharmaceutically acceptable salt thereof as an active component.

Further, the present invention provides a method for diagnosing angiogenesis-related diseases comprising a step of administering a diagnostically effective amount of tricarbonyl technetium-99m labeled cyclic RGD derivative of Formula 1 or pharmaceutically acceptable salt thereof to a subject.

Further, the present invention provides a method for treatment of angiogenesis-related diseases, comprising a step of administering a therapeutically effective amount of tricarbonyl rhenium-188 labeled cyclic RGD derivative of Formula 1 or pharmaceutically acceptable salt thereof to a subject.

The cyclic RGD derivative of Formula 1 according to the present invention is a compound in which tricarbonyl technetium-99m, tricarbonyl rhenium-188 or tricarbonyl rhenium reactant is bound to a label pocket consisting of amine and two hydroxycarbonylmethyl groups to forms an octahedral structure having three carbonyl, amine, and two hydroxyl groups centered on technetium-99m.

The cyclic RGD derivative of Formula 1 may build up monomeric, dimeric or tetrameric cyclic RGD, in which dimeric cyclic RGD dimer, when constructed, has higher affinity to integrin $\alpha_v\beta_3$, the biomarker for tumor angiogenesis, and by introducing various polyethylene glycol chains to aspartic acid, the linker between the cyclic RGD and label groups, thereby forming bivalent structure that the cyclic RGD dimer is simultaneously bindable to two integrins $\alpha_v\beta_3$, tumor image of higher resolution can be obtained and better treatment result can be obtained based on the same. It was confirmed that the compound having cyclic RGD dimer is excreted rapidly from the liver and large intestine due to the negative charge (−) of the pocket group containing tricarbonyl technetium-99m or tricarbonyl rhenium-188 cyclic RGD derivative in the vascular endothelial cells, based on the distribution in body observed on the tumor-transplanted mice. Accordingly, the higher ratio of tumor to normal organs was obtained.

Further, the cyclic RGD derivative of Formula 1 according to the present invention can have higher affinity to integrin $\alpha_v\beta_3$, the biomarker for tumor-induced angiogenesis, by constructing cyclic RGD tetramer, and by introducing various polyethylene glycol chains to aspartic acid, the linker between the cyclic RGD and label groups, the structure is formed in which the cyclic RGD tetramer can bind simultaneously to several $\alpha_v\beta_3$ integrins. As a result, tumor image of higher uptake can be obtained, and better treatment effect can be obtained based on the same.

Furthermore, the cyclic RGD derivative making up the cyclic RGD tetramer also has high affinity to $\alpha_v\beta_3$ integrin, and is excreted rapidly from the liver and large intestines due to the negative charge (−) of the pocket group contained in tricarbonyl technetium-99m or tricarbonyl rhenium-188 labeled cyclic RGD derivatives in the vascular endothelial cells.

Accordingly, the cyclic RGD derivative of Formula 1 according to the present invention has high level of affinity to integrin $\alpha_v\beta_3$, so-called vitronectin receptor, in tumor-induced angiogenesis at subnanomolar level, so that tumor image of high uptake is obtained from the tumor-transplanted animal upon initial intake of tricarbonyl technetium-99m labeled cyclic RGD derivative, with the intake rate in the liver and large intestine being markedly reduced compared to that obtained by the conventionally-known radioisotope labeled cyclic RGD derivative, according to which better imaging, and exclusive action specifically to the positive integrin $\alpha_v\beta_3$ cancer cells with activated $\alpha_v\beta_3$ integrin are provided. Further, compared to tumor animal model injected with saline solution only, rhenium-188 labeled derivative, the therapeutic radionuclide using the same precursor as the one used in technetium-99m labeling, exhibits effective tumor growth inhibition and anti-angiogenic effect when injected to tail vein. As a result, the cyclic RGD derivative of Formula 1 according to the present invention can be advantageously used as a medicine customized for the diagnosis or treatment (radiotherapy) of angiogenesis-related diseases.

The diagnosis may be performed by intravenous injection of the tricarbonyl technetium-99m labeled cyclic RGD derivative or pharmaceutically acceptable salt thereof into a subject and examining presence of antiogenesis-related disease by SPECT, and when acquiring image of cancer augiogenesis, performing customized treatment (radiotherapy) by using tricarbonyl rhenium-188 labeled cyclic RGD derivative which uses the same precursor.

In one embodiment, the angiogenesis-related disease may preferably include a disease with over expression of integrin $\alpha_v\beta_3$ such as brombosis, myocardial ischemia, solid tumor, or metastatic tumor.

The cyclic RGD derivative of Formula 1 or pharmaceutically acceptable salt thereof according to the present invention is administered by intravenous injection for clinical use, in a varying amount depending on age, weight, gender, dosage form, health condition, and severity of disease of a patient. For an adult patient weighing 70 Kg, for example, for diagnose purpose, generally, 1-20 mCi/dose, and preferably, 3-7 mCi/dose may be administered, or depending on decision by a doctor or pharmacist, administration may be divided at predetermined time intervals, for example, once per day, or several times per day. For the purpose of treatment, 1-1000 mCi/dose, and preferably, 1-500 mCi/dose may be administered, or depending on a decision by a doctor or a pharmacist, the administration may be divided at predetermined time intervals, for example, once per day or several times per day.

Further, the present invention provides cyclic RGD derivative precursor expressed by Chemical Formula 2 for labeling of tricarbonyl technetium-99m or rhenium-188.

[Chemical Formula 2]

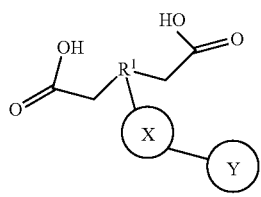

where, $R^1$, X and Y are as defined above with reference to Chemical Formula 1.

Preferably, the precursor of cyclic RGD derivative for labeling of the tricarbonyl technetium-99m or rhenium-188 may be selected from the group consisting of compounds expressed by Chemical Formulae 2A to 2C.

[Chemical Formula 2A]

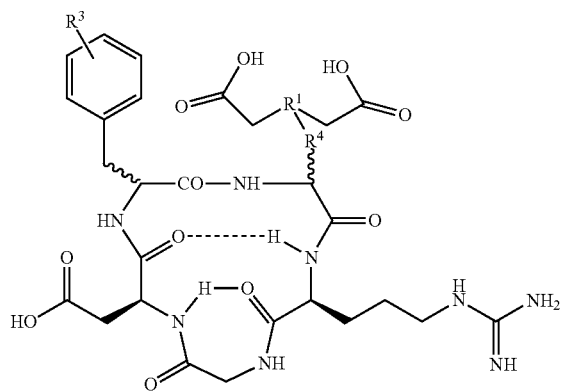

[Chemical Formula 2B]

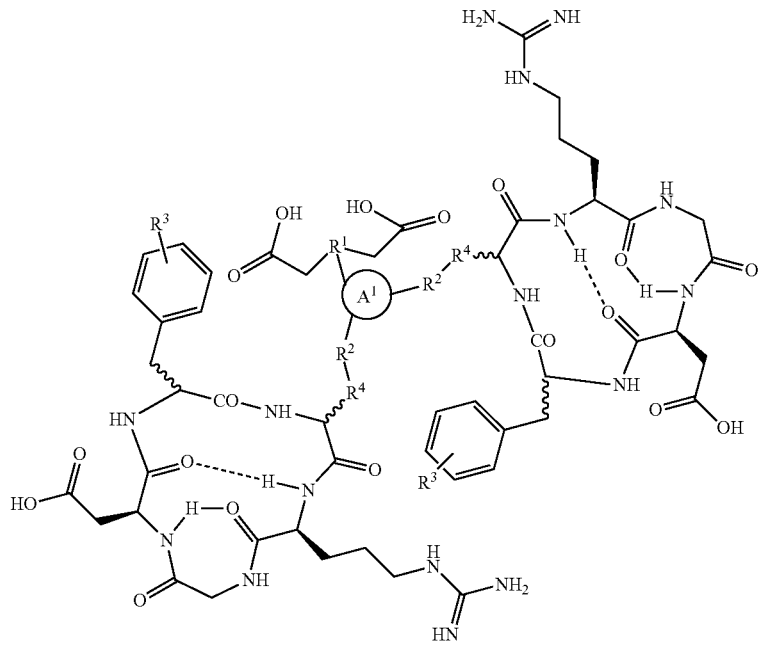

[Chemical Formula 2C]
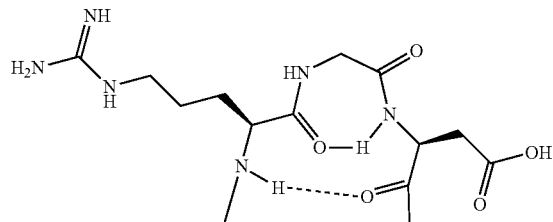
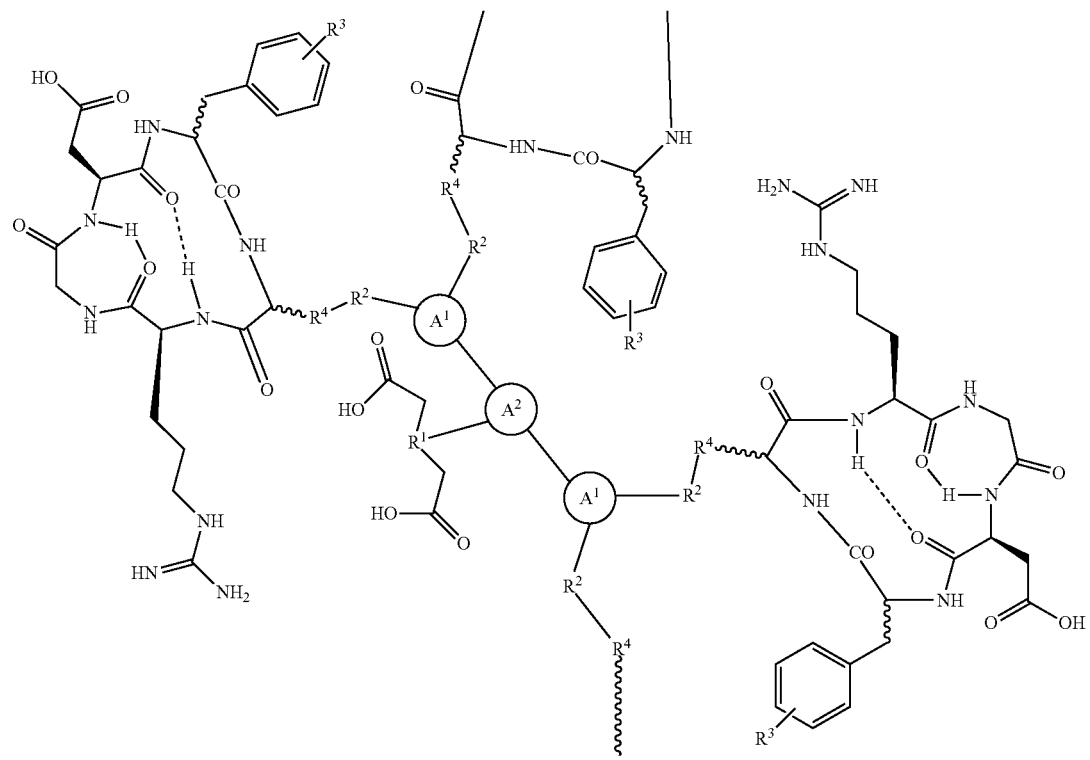
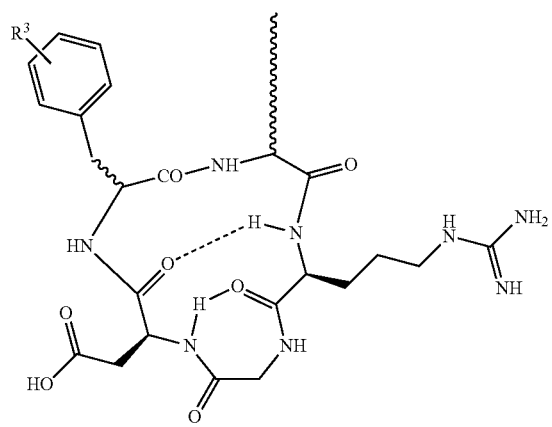

Where, M, $R^1$, $R^2$, $R^3$, $R^4$, $A^1$ and $A^2$ are as defined above with reference to Chemical Formula 1.

The preparation of the precursor of cyclic RGD derivative for labeling of the tricarbonyl technetium-99m or rhenium-188 will be explained below with reference to examples, but the present invention is not limited to the specific examples only.

Hereinbelow, the embodiment of the invention will be explained in detail with reference examples. However, the present invention is not limited to any specific example only.

Preparative Example 1

Preparation of Starting Material (3) for Precursor of Tricarbonyl Technetium-99m or Rhenium-188 Labeled Cyclic RGD Derivative

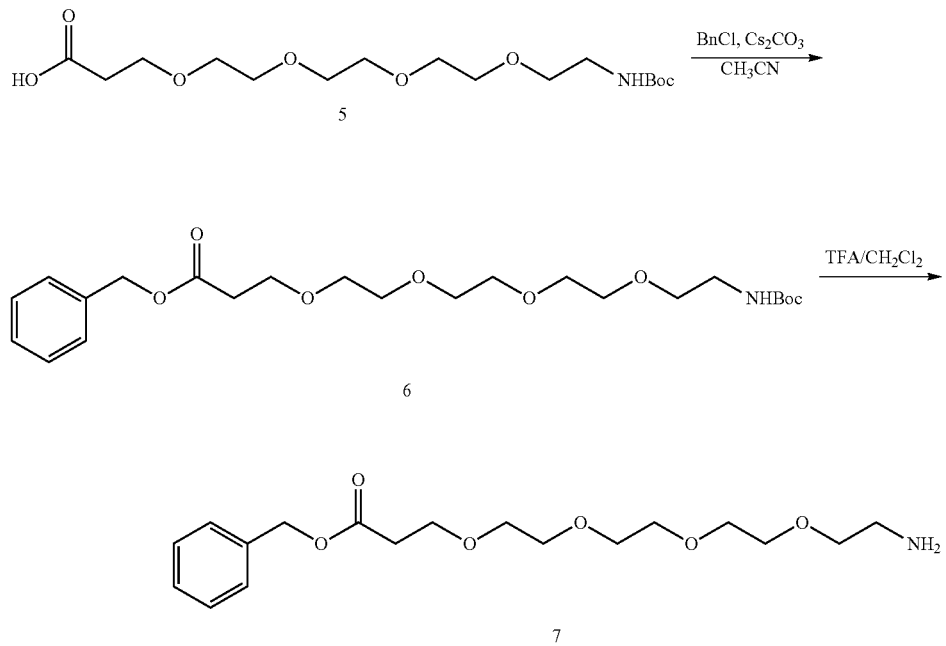

The compound of Formula 3, which is used as a starting material for a precursor of the tricarbonyl technetium-99m or rhenium-188 labeled cyclic RGD derivative according to the present invention was synthezied by referring to Haubner, R., Wester, H-J., Reuning, U., Senekowi tsch→Schmidt ke, R., Diefenbach, B., Kessler, H., Stocklin G., Schwa iger, M., J. Nucl. Med., 1999, 40: 1061-1071).

Preparative Example 2

Preparation of benzyl 1-amino-3, 6, 9, 12-tetraoxa pentadecan-15-oate (7)

(Step 1)

1-(N-(t-butyloxycarbonyl)-amino)-3, 6-9-12-tetraoxa pentadecanoate (224 mg, 0.61 mmol, 5) was dissolved in acetonitrile (5 mL) under argon gas atmosphere, cecium carbonate ($CsCO_3$, 596 mg, 1.83 mmol) and benzyl chloride (211 μL, 1.83 mmol) were added, and the reaction mixture was stirred at 80° C. for 30 minutes and cooled to room temperature. The solvent was removed under vacuum, and pure compound (6) was obtained by column chromatography.

$^1$H NMR (400 MHz, $CDCl_3$) δ 7.38-7.30 (m, 5H), 5.14 (s, 2H), 3.77 (t, J=6.4 Hz, 2H), 3.64-3.59 (m, 12H), 3.53 (t, J=5.0 Hz, 2H), 3.30 (m, 2H), 2.65 (t, J=6.4 Hz, 2H), 1.44 (s, 9H).

(Step 2)

The compound (260 mg, 0.57 mmol) of Formula 6 prepared at Step 1 was dissolved in methylene chloride (10 mL) and trifluoroacetic acid (TFA, 1 mL) was added at 0° C. After stirring for 1 hour at room temperature, saturated $NaHCO_3$ (25 mL) was added. After extraction with methylene chloride (100 mL×3) the organic layer was removed under vacuum to give benzyl 1-amino-3,6,9,12-tetraoxa pentadecan-15-oate (7).

$^1$H NMR (400 MHz, $CDCl_3$) δ 7.53 (s, 5H), 5.14 (s, 2H), 3.78 (t, J=6.2 Hz, 2H), 3.65-3.62 (m, 12H), 3.58 (t, J=4.8 Hz, 2H), 2.93 (brs, 2H), 2.66 (t, J=6.2 Hz, 2H), 2.51 (brs, 2H).

Preparative Example 3

Preparation of tricarbonyl technetium-99m or tricarbonyl rhenium-188 moiety ($^{99m}Tc(CO)_3(H_2O)_3^+$ or $^{188}Re(CO)_3(H_2O)_3^+$)

The tricarbonyl technetium-99m or rhenium-188 moiety for labeling was prepared by a method disclosed in Alberto, R., Schibli, R., Egli, A., Schubiger, A. P., Abram, U., Kaden, T. A., J. Am. Chem. Soc. 1998, 120:7987-7988; Alberto, R., Schibli, ., Schubiger, A. P., Abram, U., Pietzsch, H.-P., Johannsen, B., J. Am. Chem. Soc. 1999, 121:6076-6077; Schibli, ., Netter, M., Scapozza, L., Birr inger, M., Schel 1 ing, P., Dumas, C., Schoch, J., Schubiger, P. A., J. Organomet. Chem. 2003, 668: 67-74; Schibli, R., Schwarzbach, R., Alberto, R., Ortner, K., Schmal le, H., Dumas, C., Egli, A., Schubiger, P. A. Bioconjuate Chem. 2002, 13:750-756.

Examples 1-5

Preparation of Precursor for Tricarbonyl Technetium-99m or Rhenium-188 Labeled Cyclic RGD Derivative According to the Present Invention

Example 1

Preparation of cyclic {(tricarbonyl-N-α-bis-hydroxycarbonyl methyl-lysine)-arginin-glycine-aspartic acid-D-phenylalanine} (2a)

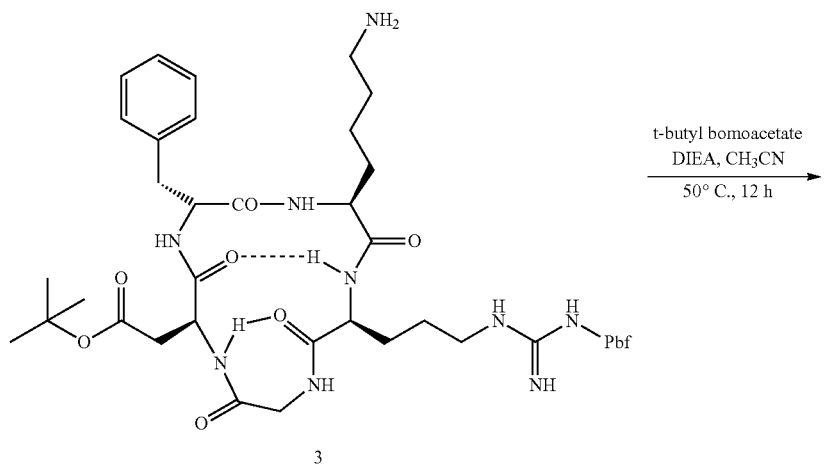

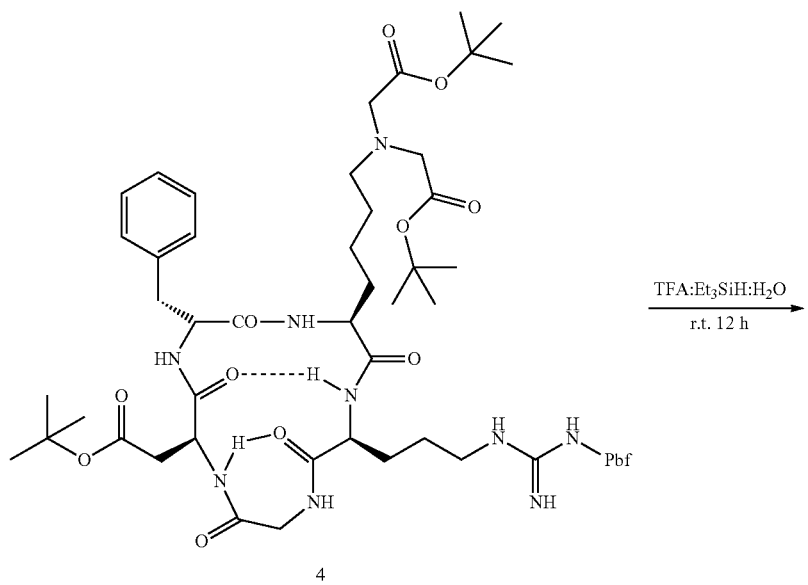

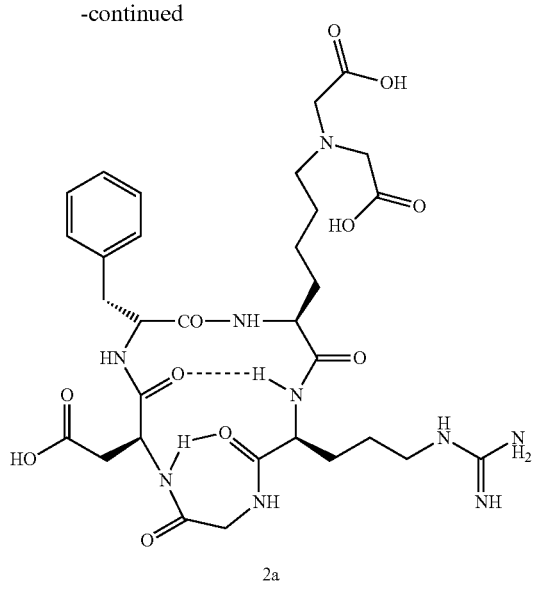

2a (Step 1)

The compound (240 mg, 0.26 mmol) of Formula 3 prepared at Preparative Example 1 and t-butyl bromoacetate (115 mL, 0.77 mmol) were dissolved in acetonitrile (CH$_3$CN, 5 mL) and N,N'-Diisopropylethylamine (DIEA, 130 μL, 0.77 mmol), and the reaction mixture was stirred for 12 hours at 50° C. The solvent was removed under vacuum and the compound of Formula 4 was isolated by column chromatography with organic solvent, methanol and dichloromethane (10:90=MeOH:CH$_2$Cl$_2$) solution.

MALDI-TOF MS (M+Na$^+$)=1163.4

(Step 2)

The compound of Formula 4 prepared at Step 1 was dissolved in TFA:Et$_3$SiH:H$_2$O (95:2.5:2.5, 10 mL). After reaction mixture was stirred at room temperature for 12 hours, the solution was entirely evaporated under vacuum, and then solid obtained by addition of diethyl ether was filtered. The resultant white solid was sufficiently washed with diethyl ether and dried. As a result, the compound of Formula 2a was prepared.

MALDI-TOF MS (M+Na$^+$)=720.8

Example 2

Preparation of cyclic {(tricarbonyl-N-α-bis-hydroxycarbonyl methyl-glycine-CONH(CH$_2$CH$_2$O)$_4$CH$_2$CH$_2$CONH-lysine)-alginine-glycine-aspartic acid-D-phenylalanine} (2b)

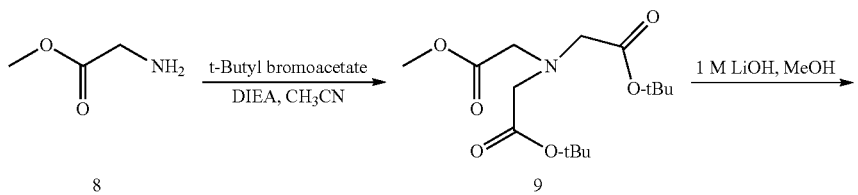

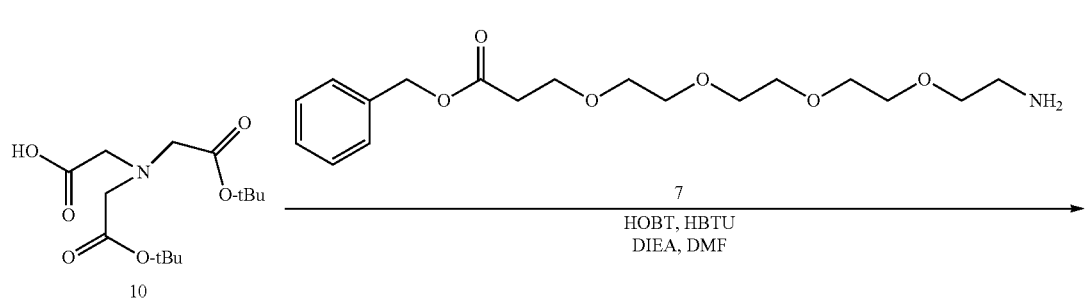

-continued
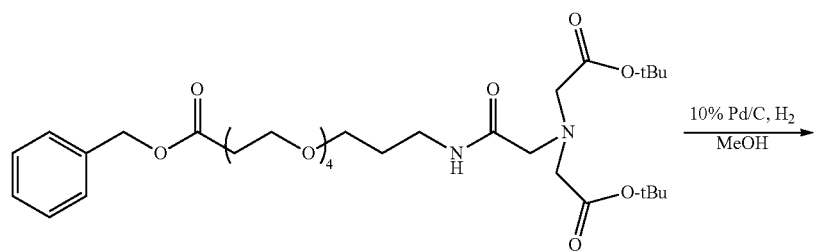
11
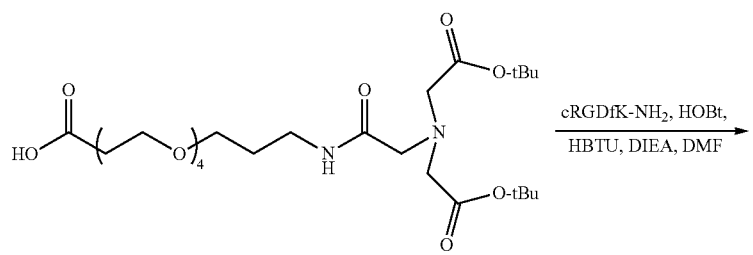
12
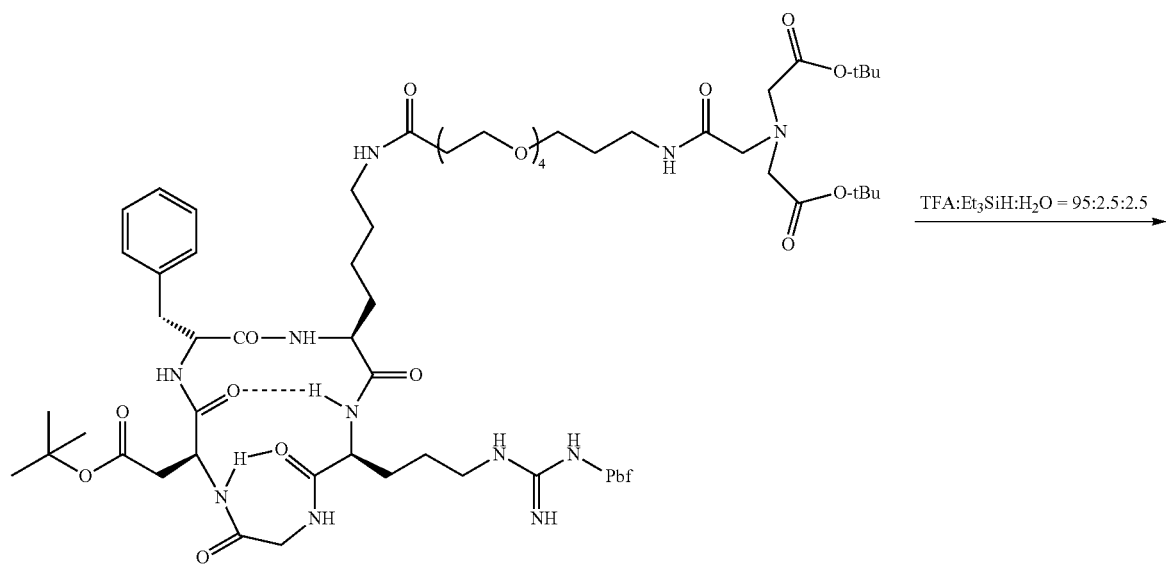
13

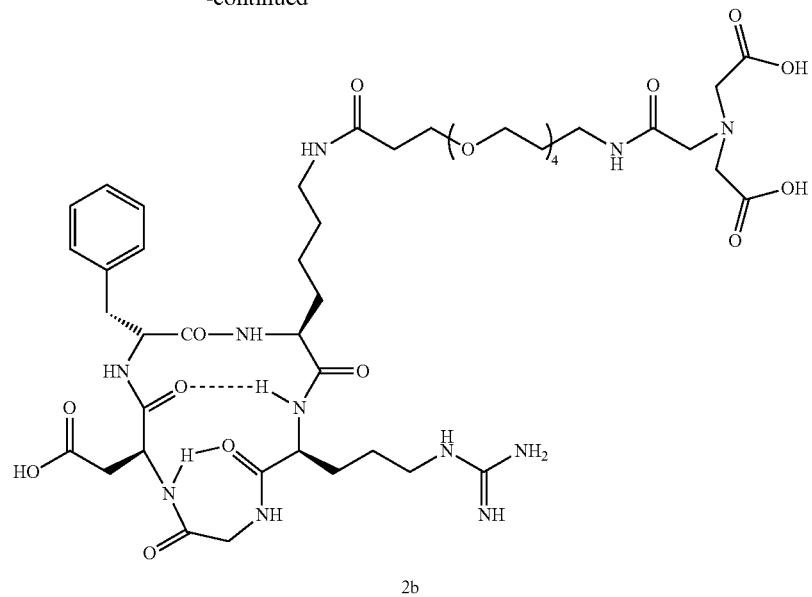

2b (Step 1)

The compound of Formula 9 was prepared with the method of Step 1 at Example 1, except for the difference of using glycine-methylester-hydrochloride of Formula 8 instead of the compound of Formula 3.

$^1$H NMR (400 MHz, CDCl$_3$) δ 3.71 (s, 3H), 3.64 (s, 2H), 3.53 (s, 4H), 1.44 (s, 18H).

(Step 2)

The compound (550 mg, 1.73 mmol) of Formula 9 prepared at Step 1 was dissolved in methanol (MeOH, 10 mL), and 1 M lithium hydroxide (1 M LiOH, 3.4 mL, 3.4 mmol) was added. After stirring at 50° C. for 1 hour, 1 N hydrochloric acid (1 N HCl, 3.8 mL, 2.2 mmol) was added to neutralize. With the removal of solvent under vacuum, the compound of Formula 10 was obtained.

$^1$H NMR (400 MHz, CDCl$_3$) δ 3.48 (s, 2H), 3.47 (s, 4H), 1.48 (s, 18H).

(Step 3)

The compound (60 mg, 0.19 mmol) of Formula 10 prepared at Step 2, along with N-hydroxy benzotriazole (51 mg, 0.38 mmol), and 0-benzotriazole-N,N,N',N'-tetramethyl-uronium-hexafluorophosphate (144 mg, 0.38 mmol) were dissolved in N,N'-dimethylformamide (5 mL) under argon. After stirring for 30 minutes, the compound (47 mg, 0.13 mmol) of Formula 7 prepared at Preparative Example 2 and N,N'-diisopropylethylarmine (133 mL, 0.762 mmol) were added and stirred at room temperature for 16 hours. N,N'-dimethylformamide was removed under vacuum, and the target compound (11) was obtained via isolation by column chromatography.

$^1$H NMR (400 MHz, CDCl$_3$) δ 8.09 (brs), 7.34 (brs, 5H), 5.13 (s, 2H), 3.76-3.36 (m, 22H), 2.65-2.64 (m, 2H), 1.45 (s, 18H).

(Step 4)

The 10% palladium charcoal (10% Pd/C, 34 mg, 0.032 mmol) was added under nitrogen atmosphere, and the compound (70 mg, 0.11 mmol) of Formula 11 of Step 3 dissolved in methanol (5 mL) was added to the reaction mixture. The interior of the reaction container was converted to hydrogen gas and stirring was performed at room temperature under hydrogen gas for 16 hours. Palladium was filtered out through celite filter, and the target compound (12) was obtained by removing methanol under vacuum.

$^1$H NMR (400 MHz, CDCl$_3$) δ 9.02 (brs), 8.20 (brs), 3.75-3.70 (m, 2H), 3.63-3.56 (m, 14H), 3.52-3.47 (m, 2H), 3.38-3.36 (m, 2H), 2.57 (t, J=6.0 Hz), 1.44 (s, 18H).

(Step 5)

The target compound (13) was prepared by the same method of Step 5 at Example 2, except for the difference of using the compound of Formula 12 at Step 4 and the compound of Formula 3 at Preparative Example 1 as reacting materials.

ESI MS (M+H$^+$)=1444.7

(Step 6)

The target compound (2b) was prepared by the same method as that of Step 1 at Example 1, except for the difference of using the compound of Formula 13 at Step 5 as a starting material.

ESI MS (M+H$^+$)=1024.5.

Example 3
Preparation of (tricarbonyl-N-α-bis-hydroxycarbonyl methyl-aspartic acid)-[cyclic (lysine-alginine-glycine-aspartic acid-D-phenylalanine)]₂ (2c)
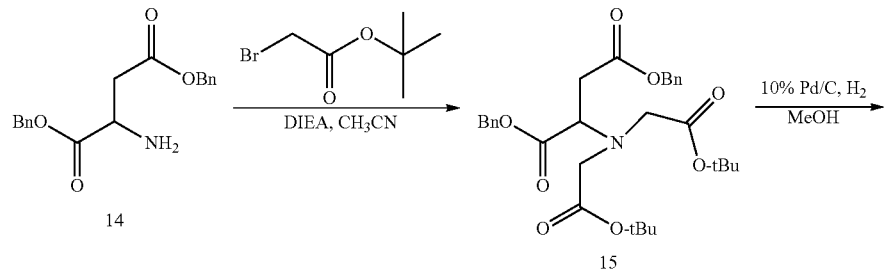
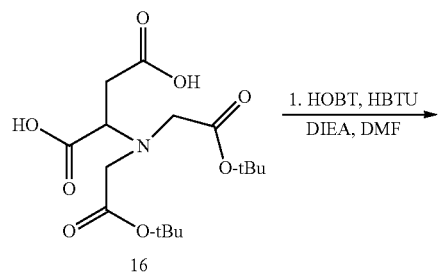
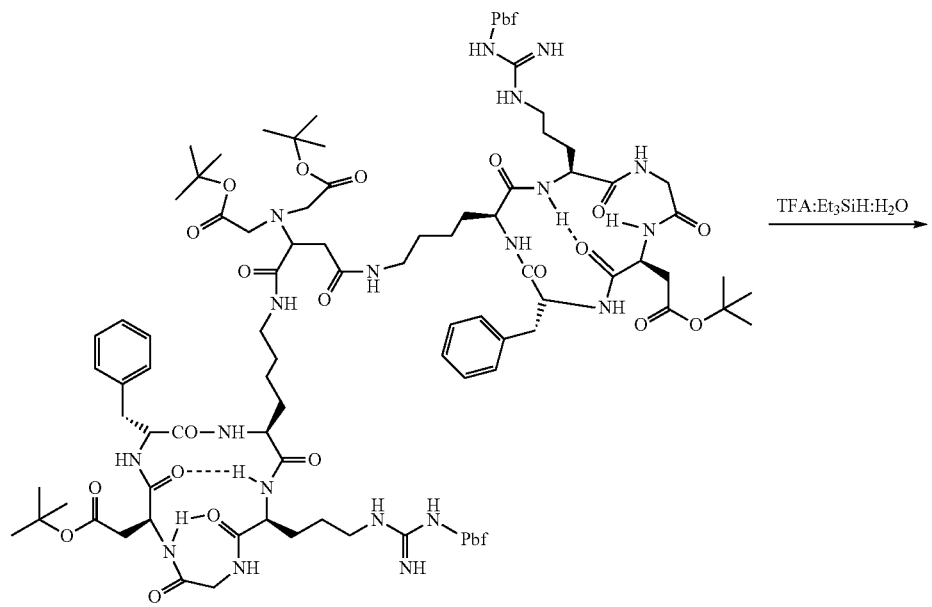

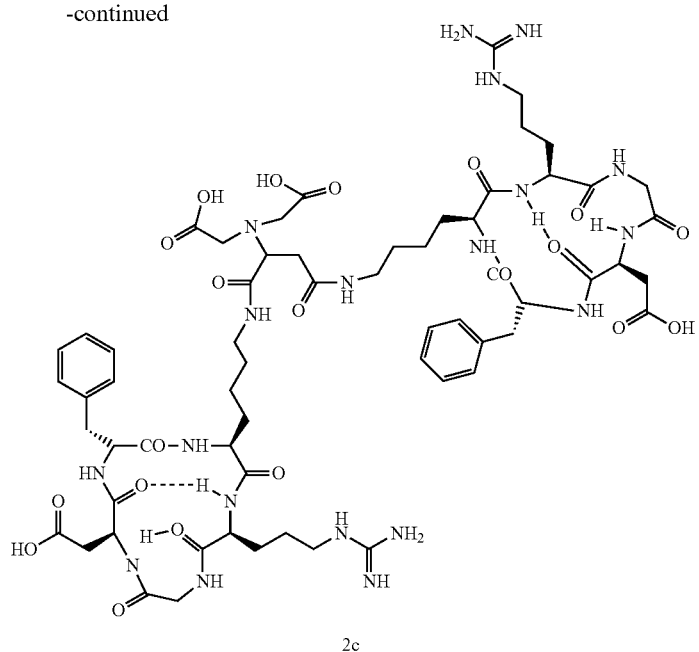

2c (Step 1)

The target compound (15) was prepared by the same method as that of Step 1 at Example 1, except for the difference of using O,O'-dibenzyl aspartic acid hydrochloride as a starting material.

$^1$H NMR (400 MHz, CDCl$_3$) δ 7.36-7.26 (m, 10H), 5.14-5.06 (m, 4H), 3.99 (dd, J=9.2, 5.2 Hz, 1H), 3.61-3.50 (m 4H), 2.94 (dd, J=16.8, 9.6 Hz, 1H), 2.82 (dd, J=16.4, 5.6 Hz, 1H), 1.42 (s, 18H).

(Step 2)

The target compound (16) was prepared by the same method of Step 2 at Example 2, except for the difference of using the compound of Formula 15 at Step 1 as a starting material.

$^1$H NMR (400 MHz, CDCl$_3$) δ 9.60 (brs, 2H), 3.90 (t, J=6.6 Hz, 1H), 3.55-3.40 (m, 4H), 2.98 (dd, J=16.4, 5.2 Hz, 1H), 2.66 (dd, J=16.8, 7.6 Hz, 1H), 1.46 (s, 18H).

(Step 3)

The target compound (17) was prepared by the same method of Step 5 at Example 2, except for the difference of using the compound of Formula 16 at Step 2 as a starting material.

MALDI-TOF MS (M+Na$^+$)=2171.06

(Step 4)

The target compound (2c) was prepared by the same method as that of Step 2 atf Example 1, except for the difference of using the compound of Formula 17 at Step 3 as a starting material.
ESI MS (M+H$^+$)=1420.5

Example 4

Preparation of {tricarbonyl-N-α-bis-hydroxycarbonyl methyl-aspartic acid}-{(polyethylene glycol)4-[cyclic (lysine-alginine-glycine-aspartic acid-D-phenylalanine)]}$_2$ (2d)

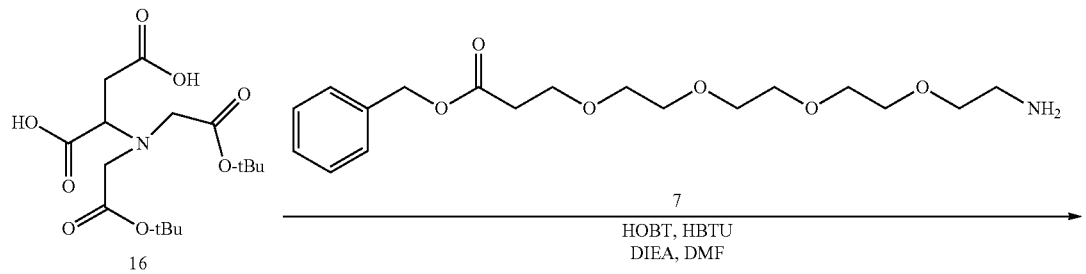

-continued
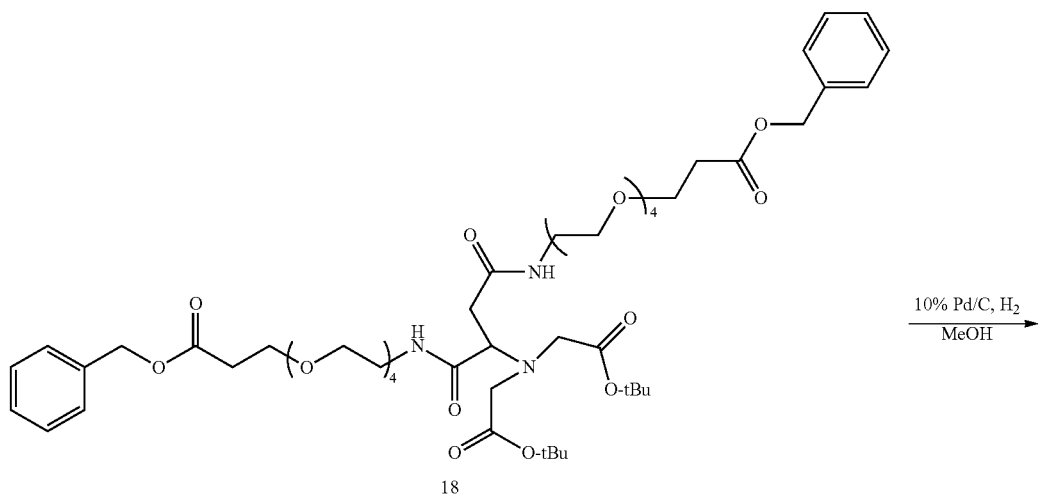
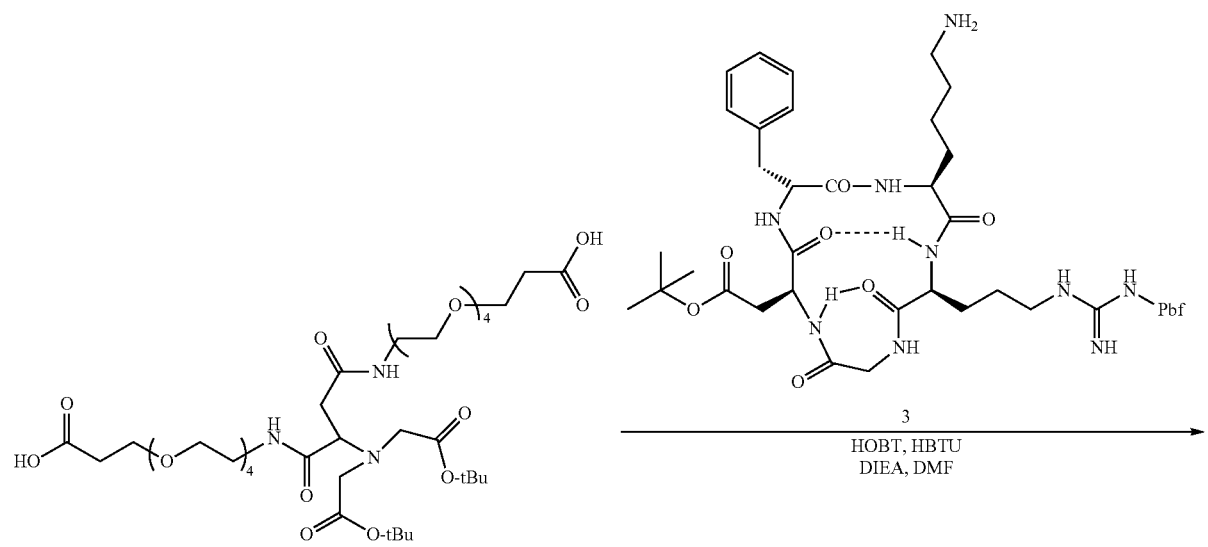

-continued
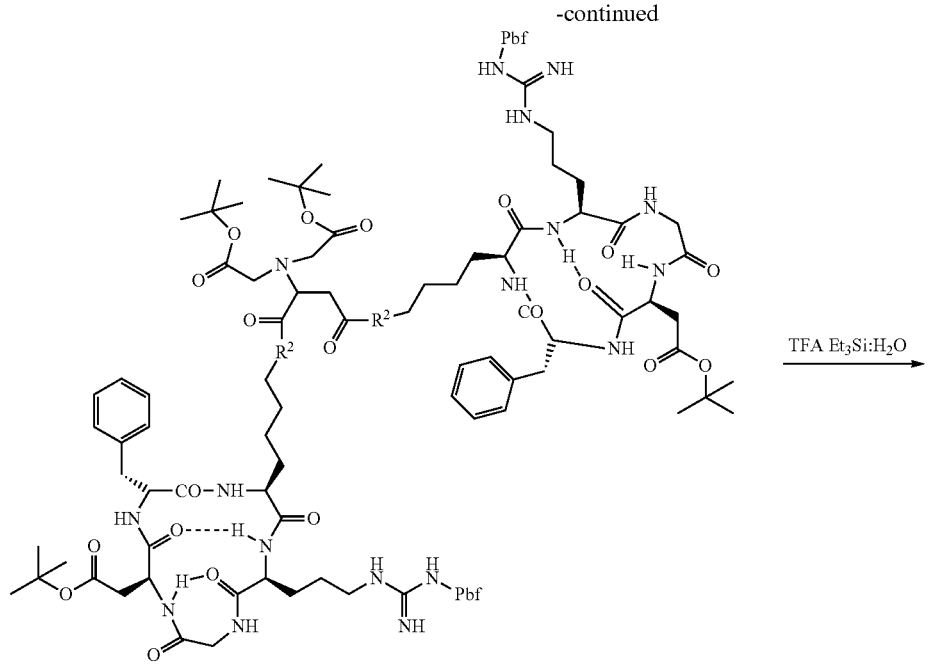
20
R² = NH(CH₂CH₂O)₄CH₂CH₂CONH.
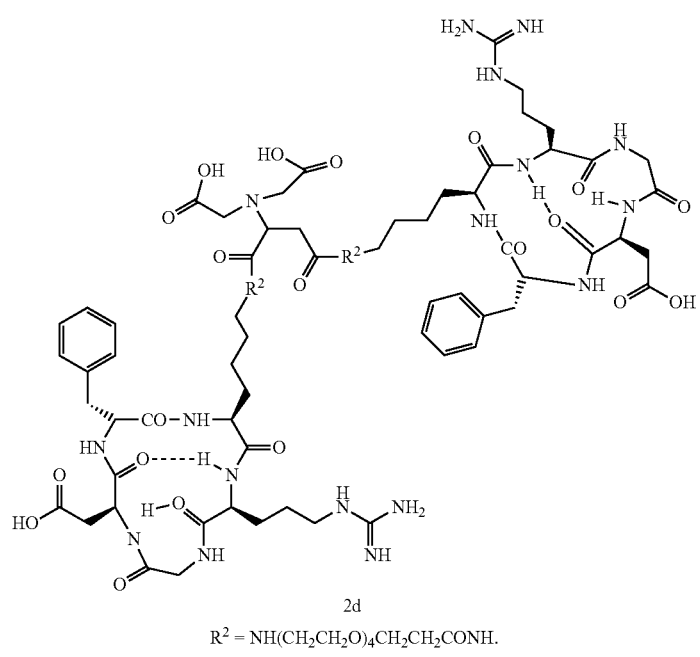
2d
R² = NH(CH₂CH₂O)₄CH₂CH₂CONH.

(Step 1)

The compound of Formula 18 was prepared by the same method as that of Step 5 at Example 2, except for the difference of using the compound of Formula 16 as a starting material instead of the compound of Formula 3.

$^1$H NMR (400 MHz, CDCl$_3$) δ 8.46 (brt, 1H), 7.38-7.30 (m, 10H), 6.84 (brs, 1H), 5.13 (s, 4H), 3.87 (t, J=6.4 Hz, 1H), 3.77 (t, J=6.4 Hz, 4H), 3.63-3.61 (m, 24H), 3.57-3.53 (m 4H), 3.51-3.42 (m 6H), 3.31-3.27 (m, 2H), 2.81 (dd, J=10.8, 6.4 Hz, 1H), 2.65 (t, J=6.6 Hz, 4H), 2.38 (dd, J=14.8, 6.4 Hz, 1H), 1.44 (s, 18H).

(Step 2)

The compound of Formula 19 was prepared by the same method as that of Step 6 of Example 2, except for the difference of using the compound of Formula 18 at Step 1 as a starting material.

$^1$H NMR (400 MHz, CDCl$_3$) δ 8.57 (brt, 1H), 7.82 (brs, 1H), 5.13 (s, 4H), 3.92 (t, J=6.6 Hz, 1H), 3.77-3.70 (m, 4H), 3.64-3.55 (m, 31H), 3.47-3.30 (m 2H), 3.34-3.29 (m 3H), 2.81 (dd, J=22, 7.2 Hz, 1H), 2.59 (t, J=12 Hz, 4H), 2.46 (dd, J=20.4, 5.2 Hz, 1H), 1.45 (s, 18H).

(Step 3)

The compound of Formula 20 was prepared by the same method as that of Step 5 at Example 2, except for the difference of using the compound of Formula 19 at Step 2 and the compound of Formula 3 at Preparative Example 1 as starting materials.

MALDI-TOF MS (M+Na$^+$)=2665.87

(Step 4)

The target compound (2d) was prepared using the same method as that of Step 2 at Example 1, except for the difference of using the compound of Formula 20 at Step 3 as a starting material.

MALDI-TOF MS (M+Na$^+$)=1914.65

Example 5

Preparation of {tricarbonyl-N-α-bis-hydroxycarbonyl methyl-(polyethylene glycol)-4-aspartic acid}-[cyclic(lysine-alginine-glycine-aspartic acid-D-phenylalanine)]$_2$ (2e)

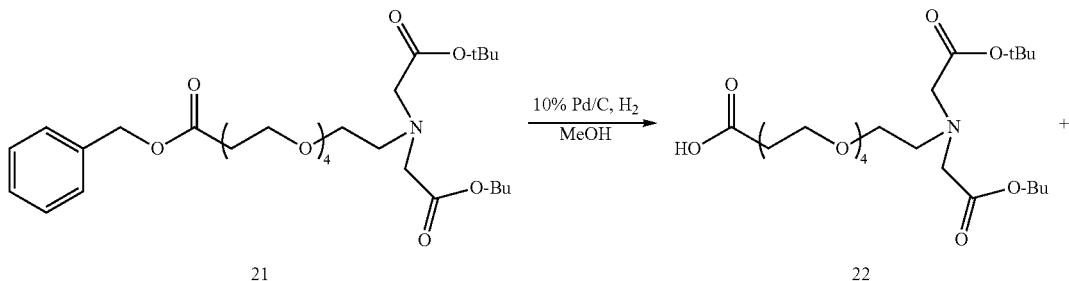

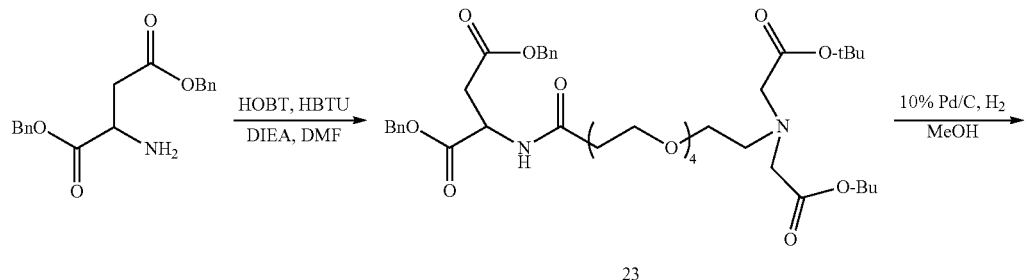

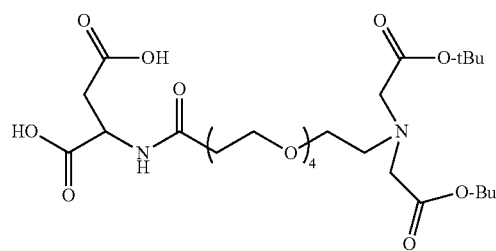

-continued
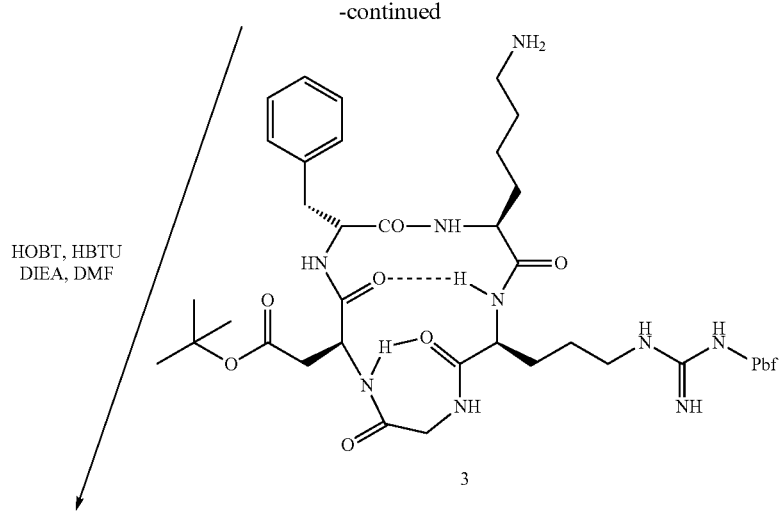
3
HOBT, HBTU
DIEA, DMF
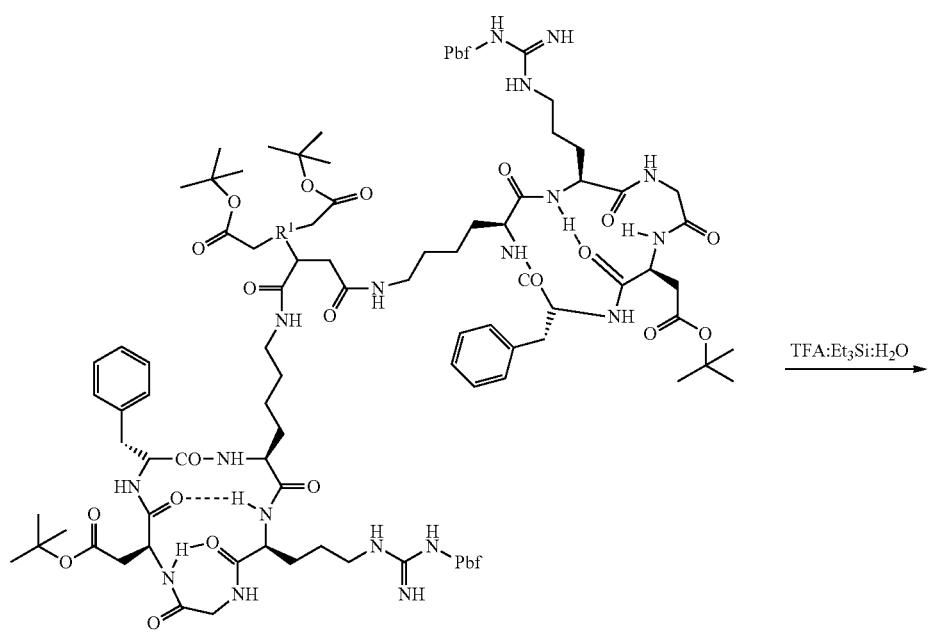
25
R² = N or N(CH₂CH₂O)₄CH₂CH₂CONH,
n = 4

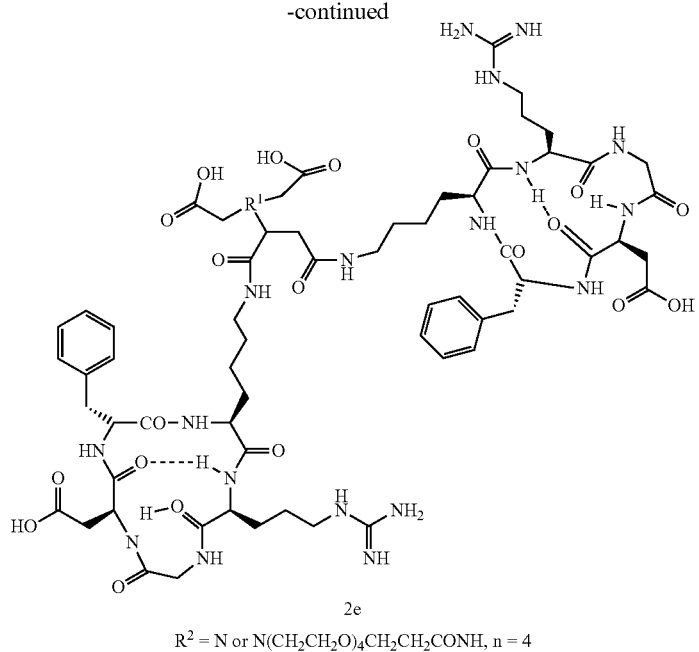

2e

R² = N or N(CH₂CH₂O)₄CH₂CH₂CONH, n = 4

(Step 1)

The compound of Formula 21 was prepared using the same method as that of Step 1 at Example 1, except for the difference of using the compound of Formula 7 at Preparative Example 2 as a starting material.

¹H NMR (400 MHz, CDCl₃) δ 7.37-7.34 (m, 5H), 5.14 (s, 4H), 3.77 (t, J=6.4 Hz, 2H), 3.63-3.58 (m, 14H), 3.49 (s 4H), 2.94 (t, J=5.8 Hz 2H), 2.65 (t, J=6.6 Hz 2H), 1.45 (s, 18H).

(Step 2)

The compound of Formula 22 was prepared using the same method as that of Step 6 at Example 2, except for the difference of using the compound of Formula 21 prepared at Step 1 as a starting material.

¹H NMR (400 MHz, CDCl₃) δ 7.97 (brs, 1H), 3.74 (t, J=5.8 Hz, 2H), 3.64-3.60 (m, 14H), 3.50 (s, 4H), 2.95 (t, J=5.0 Hz, 2H), 2.57 (t, J=5.6 Hz, 2H), 1.44 (s, 18H).

(Step 3)

The compound of Formula 23 was prepared using the same method as that of Step 5 at Example 2, except for the difference of using the compound of Formula 22 prepared at Step 2 and O,O'-dibenzyl aspartic acid hydrochloride as starting materials.

¹H NMR (400 MHz, CDCl₃) δ 7.36-7.27 (m, 10H), 5.13 (d, J=1.6 Hz, 2H), 5.06 (d, J=0.8 Hz, 2H), 4.94-4.90 (m, 1H), 3.67 (t, J=5.8 Hz, 2H), 3.64-3.55 (m, 14H), 3.47 (s, 4H), 3.06 (dd, J=22, 4.8 Hz, 1H), 2.94-2.87 (m, 3H), 2.49 (td, J=6.8, 2.0 Hz, 2H), 1.44 (s, 18H).

(Step 4)

The compound of Formula 24 was prepared using the same method as that of Step 6 at Example 2, except for the difference of using the compound of Formula 23 at Step 3 as a starting material.

¹H NMR (400 MHz, CDCl₃) δ 9.49 (brs, 1H), 7.61 (brd, J=4.4 Hz, 1H), 4.69 (brs, 1H), 3.68-3.41 (m, 20H), 2.99-2.94 (m, 3H), 2.78 (dd, J=24, 7.2 Hz, 1H), 2.52 (brs, 1H), 1.45 (s, 18H).

(Step 5)

The compound of Formula 25 was prepared using the same method as that of Step 5 at Example 2, except for the difference of using the compound of Formula 24 prepared at Step 4 and the compound of Formula 3 prepared at Preparative Example 1 as starting materials.

MALDI-TOF MS (M+Na⁺)=2418.70

(Step 6)

The compound of Formula (2e) was prepared using the same method as that of Step 2 at Example 1, except for the difference of using the compound of Formula 25 at Step 5 as a starting material.

MALDI-TOF MS (M+H⁺)=1667.8

Example 6

Preparation of cyclic{(tricarbonyl-[$^{185/187}$Re]rhenium-N-α-bis-hydroxycarbonyl methyl-alginine-glycine-aspartic acid-D-phenylalanine}

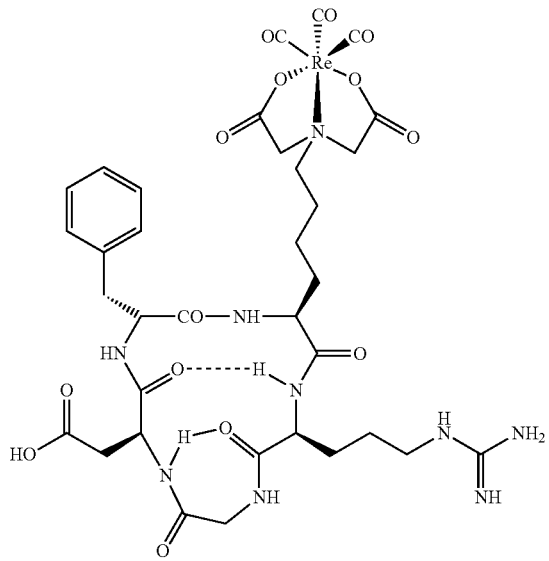

The precursor compound (2.6 mg, 0.002 mmol) of Formula 2a prepared at Example 1 and bis-(N-tetraethyl)-tribromotricarbonyl rhenium ((NEt$_4$)$_2$ReBr$_3$(CO)$_3$, 1.6 mg, 0.0025 mmol) were dissolved in water:methanol (v/v=1/1, 1 mL). After stirring for 1 h and 20 min, solvent was removed using nitrogen gas. The target compound dissolved in water was purified using HPLC and the target compound was analyzed using MALDI-TOF mass spectrometry.

(MALDI-TOF MS (M+H$^+$)=990.85).

For HPLC, mobile phase was acetonitrile (20%)/distilled water (80%) containing 0.1% trifluoroacetic acid, and mobile phase was increased to 90:10 at 30 minutes, and HPLC column was C18 column (YMC, 5 µm, 10×250 mm). The mobile phase was flowed 2 mL per minute. The target compound of Example 6 was cetected at 21.8 min as a result of detection at a UV-detector (214 nm, UV).

Example 7

Preparation of cyclic{(tricarbonyl-[$^{185/187}$Re]rhenium-N-α-bis-hydroxycarbonyl methyl-glycine-CONH(CH$_2$CH$_2$O)$_4$CH$_2$CH$_2$CONH-lysine)-alginine-glycine-aspartic acid-D-phenylalanine}

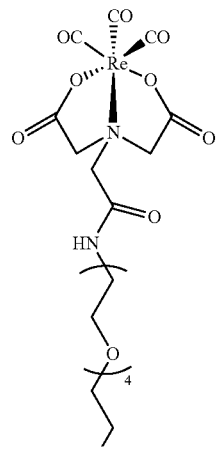
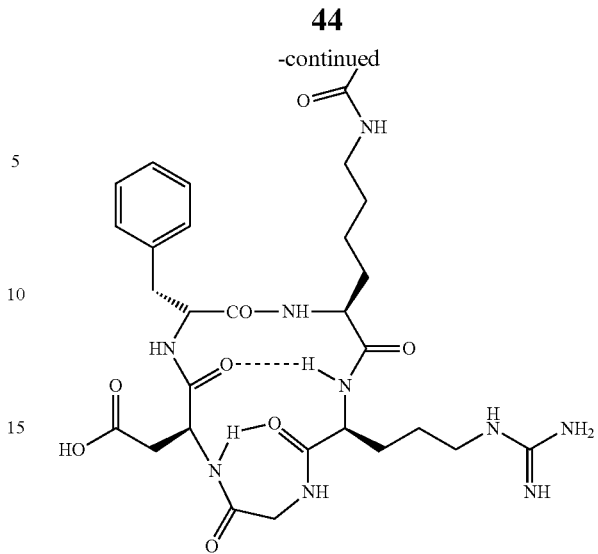

The target compound was synthesized using the same method as that of Example 6, except for the difference of using the precursor compound of Formula 2b prepared at Example 2 instead of precursor compound of Formula 2a prepared at Example 1, and the target compound was analyzed with MALDI-TOF mass spectrometry. (MALDI-TOF MS (M+H$^+$)=1293.4).

The same condition for HPLC separation as the one explained above at Example 6 was used for the isolation, and the target compound of Example 7 was detected at 21.6 min by UV-detector (214 nm).

Example 8

Preparation of (tricarbonyl-[$^{185/187}$Re]rhenium-N-α-bis-hydroxycarbonyl methyl-aspartic acid)-[cyclic (lysine-alginine-glycine-aspartic acid-D-phenylalanine)]$_2$

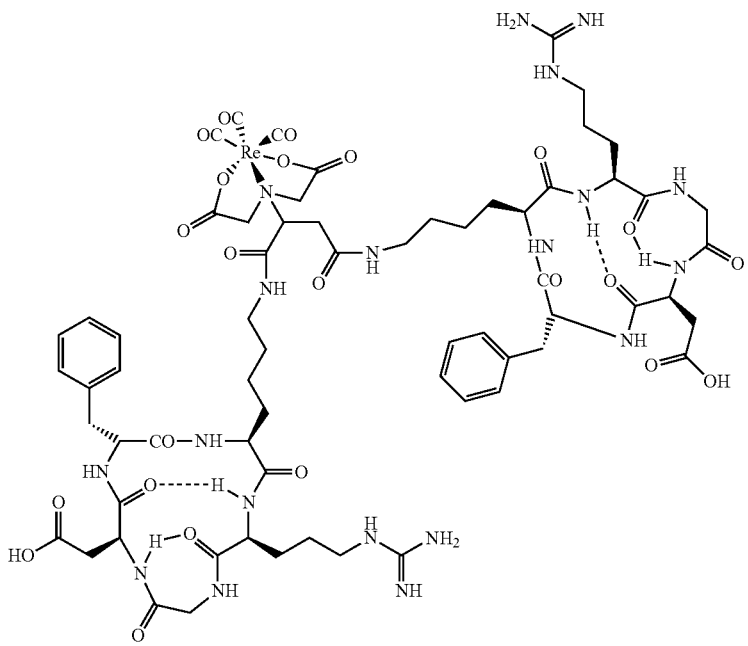

The target compound was synthesized using the same method as that of Example 6, except for the difference of using the precursor compound of Formula 2c prepared at Example instead of precursor compound of Formula 2a prepared at Example 1, and the target compound was analyzed with ESI mass spectrometry. (ESI MS (M+H⁺)=1688.5).

The same condition for HPLC separation as the one explained above at Example 6 was used for the isolation, and the target compound of Example 8 was detected at 19.2 min by UV-detector (214 nm).

Example 9

Preparation of (tricarbonyl-[$^{185/187}$Re]rhenium-N-α-bis-hydroxycarbonyl methyl-glycine-CONH (CH₂CH2O)₄CH₂CH2CONH-lysine)-[cyclic(lysine-alginine-glycine-aspartic acid-D-phenylalanine)]₂

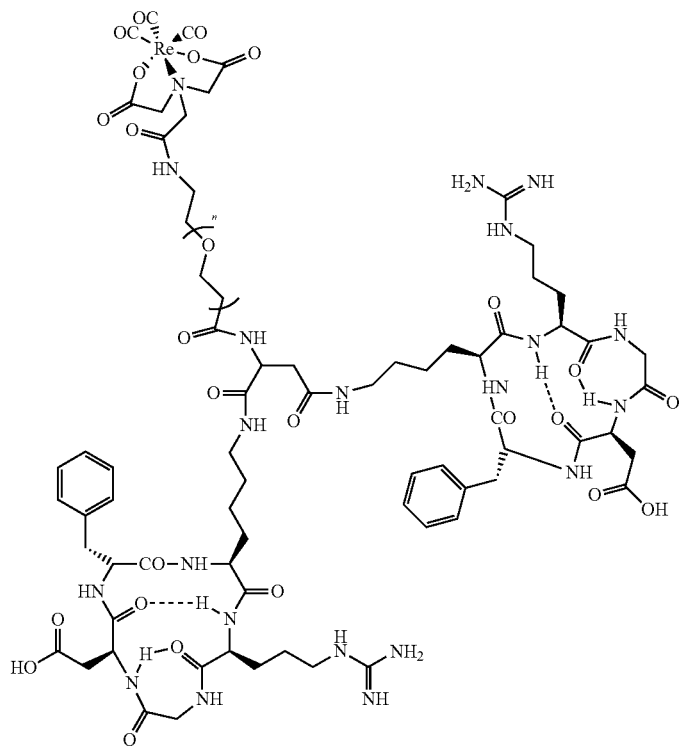

n = 4

The target compound was synthesized using the same method as that of Example 6, except for the difference of using the precursor compound of Formula 2e prepared at Example instead of precursor compound of Formula 2a prepared at Example 1, and the target compound was analyzed with ESI mass spectrometry. (ESI MS (M+H⁺)=2007.7).

The same condition for HPLC separation as the one explained above at Example 6 was used for the isolation, and the target compound of Example 9 was detected at 20.8 min by UV-detector (214 nm).

Example 10

Preparation of cyclic{(tricarbonyl-[188Re]rhenium-N-α-bis-hydroxycarbonyl methyl-lysine)-alginine-glycine-aspartic acid-D-phenylalanine}

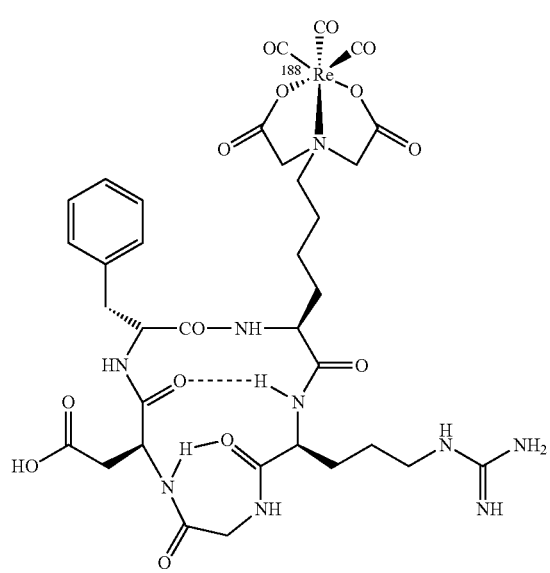

Ammoniumboran ($NH_2$—$BH_3$ complex, 5 mg) was added into 10 mL vial with rubber cap. After CO gas was introduced for 10 minutes, and then phosphoric acid ($H_3PO_4$, 6 µL) and $^{188}ReO_4^-$ (10 mCi, 1 mL) were added. After stirring at 60° C. for 15 minutes, with a 20 mL empty syringe inserted to minimize internal pressure, reaction was completed. After cooling to room temperature, 100 mM of PBS (200 µL) and saturated sodium bicarbonate (50 µL) were added to neutralize, and accordingly, rhenium tricarbonyl compound [$^{188}Re(H_2O)_3(CO)_3^+$] was synthesized, and the synthesis of reaction compound was confirmed through Radio-TLC.

[$^{188}Re(H_2O)_3(CO)_3^+$] and the precursor compound (0.5 mg) of Formula 2a prepared at Example 10 were added, heated at 75° C. for 60 minutes, and cooled in ice water. After purification through tC18 Sep-Pak cartridge, the collected solution was purified by HPLC.

For HPLC, the same condition as the one at Example 6 was applied, and the target compound of Example 10 was detected at 21.8 minute by a gamma-ray detector (NaI). This was in agreement with the retention time at the detector (UV 214 nm) of compound of Example 6. The radiochemical yield was achieved 50-60% (decay corrected), with the radiochemical purity exceeding 97%.

Example 11

Preparation of cyclic{(tricarbonyl-[188Re]rhenium-N-α-bis-hydroxycarbonyl methyl-glycine-CONH($CH_2CH_2O)_4CH_2CH_2CONH$-lysine)-alginine-glycine-aspartic acid-D-phenylalanine}

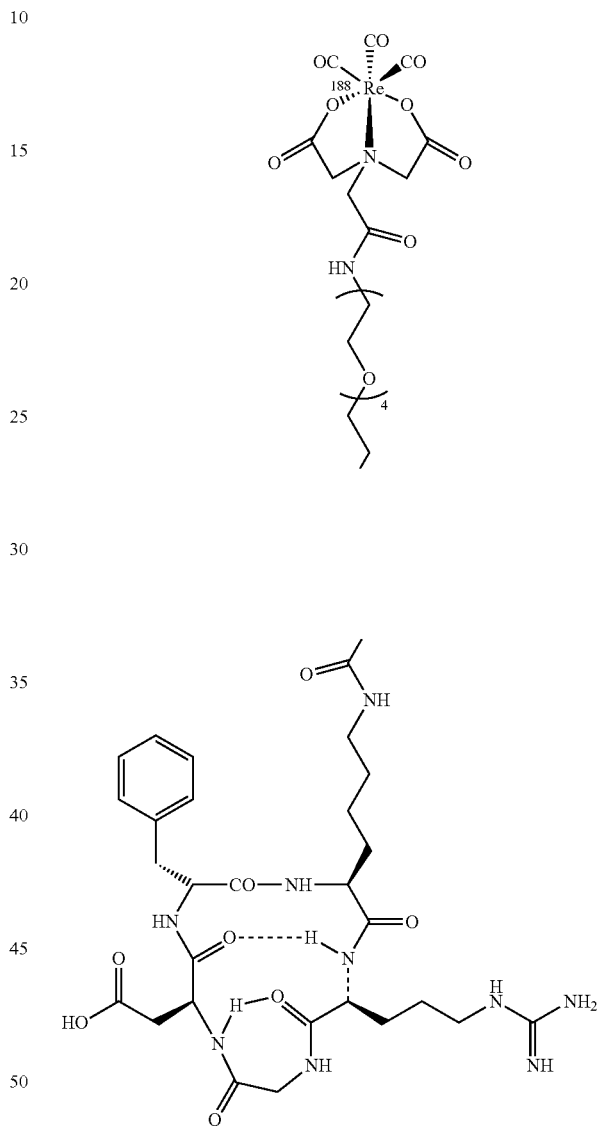

The target compound was prepared by the same method as the one applied in Example 11, except for using the precursor compound of Formula 2b at Example 2 instead of the precursor compound of formula 2a at Example 1.

For HPLC, the same condition as the one at Example 6 was applied, and the target compound of Example 11 was detected at 21.6 minute by a gamma-ray detector (NaI). This was in agreement with the retention time at the detector (UV 214 nm) of compound at Example 7. The radiochemical yield was achieved 50-60% (decay corrected), with the radiochemical purity exceeding 97%.

Example 12
Preparation of (tricarbonyl [$^{188}$Re]rhenium-N-α-bis-hydroxycarbonyl methyl-aspartic acid)-[cyclic(lysine-alginine-glycine-aspartic acid-D-phenylalanine)]$_2$

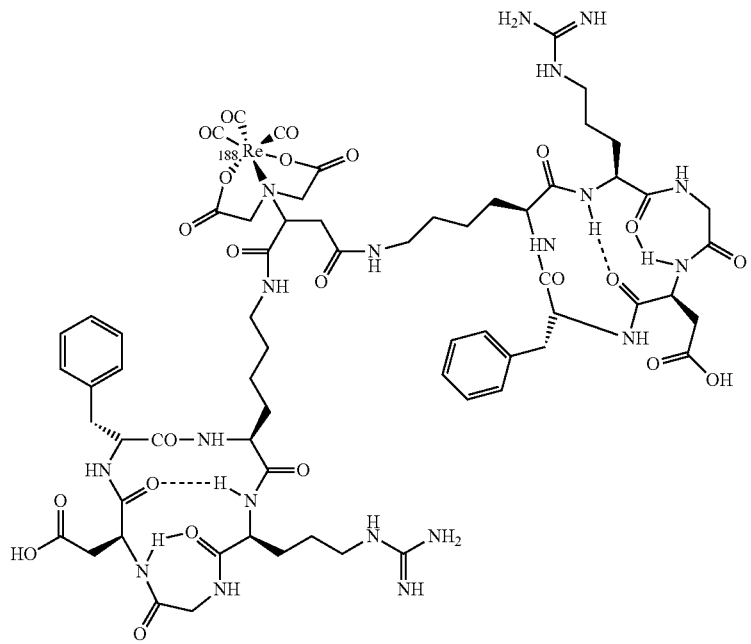

The target compound was prepared by the same method as the one applied in Example 12, except for using the precursor compound of Formula 2c at Example 3 instead of the precursor compound of formula 2a at Example 1.

For HPLC, the same condition as the one at Example 6 was applied, and the target compound of Example 12 was detected at 19.2 minute by a gamma-ray detector (NaI). This was in agreement with the retention time at the detector (UV 214 nm) of compound at Example 8. The radiochemical yield was achieved 50-60% (decay corrected), with the radiochemical purity exceeding 97%.

Example 13
Preparation of cyclic{(tricarbonyl-[$^{99m}$Tc]technetium-N-α-bis-hydroxycarbonyl methyl-alginine-glycine-aspartic acid-D-phenylalanine}

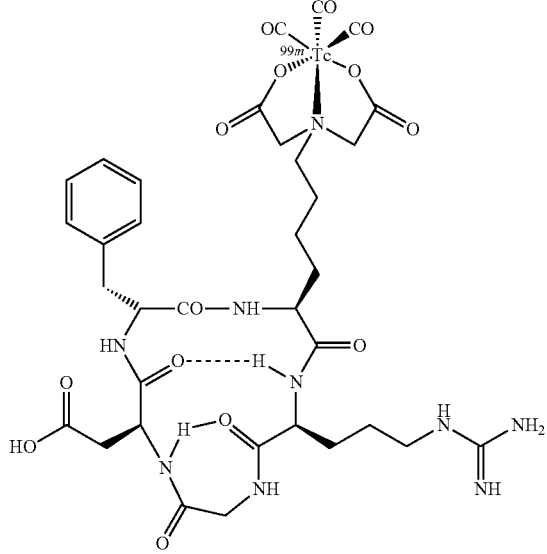

Sodium carbonate (Na$_2$CO$_3$, 4 mg), sodium borohydride (NaBH$_4$, 5.5 mg) and sodium L-tartrate dehydrate (5 mg) were added into 10 mL vial with rubber cap, and CO gas was introduced for 10 minutes. TcO$_4^-$ (10 mCi, 1 mL) from the generator was added through a syringe, and a 20 mL empty syringe was inserted to the rubber cap to minimize internal pressure. The vial was heated at 75° C. for 25 minutes. After cooling in ice water, 100 mM of phosphate buffer saline (PBS, 200 μL) and 1 N HCl (180 L) were added to neutralize. The synthesis of tricarbonyl technetium-99m compound [$^{99m}$Tc(H$_2$O)$_3$(CO)$_3^+$] was confirmed through Radio-TLC. [$^{99m}$Tc(H$_2$O)$_3$(CO)$_3^+$] and the precursor compound (0.5 mg) of Formula 2a prepared at Example 1 were added, heated at 75° C. for 60 minutes, and cooled in ice water. After purification through tC18 Sep-Pak cartridge, the collected solution was purified by HPLC.

For HPLC, mobile phase was acetonitrile (20%)/distilled water (80%) containing 0.1% trifluoroacetic acid, and mobile phase was increased to 90:10 at 30 minutes, and HPLC column was used semi-preparative C18 column (YMC, 5 μm, 10×250 mm). The mobile phase was flowed 2 mL per minute. The target compound of Example 6 was detected at 20.6 min as a result of detection at a UV-detector (214 nm). Accordingly, a one-minute difference was noticed from the retention time (21.8 minute) of detecting target compound of Example 13 at the detector (UV 214 nm). The radiochemical yield after was achieved 60-70%, with the radiochemical purity exceeding 97%.

Example 14

Preparation of cyclic{(tricarbonyl-[$^{99m}$Tc]technetium-N-α-bis-hydroxycarbonyl methyl-glycine-CONH(CH$_2$CH$_2$O)$_4$CH$_2$CH$_2$CONH-lysine)-alginine-glycine-aspartic acid-D-phenylalanine}

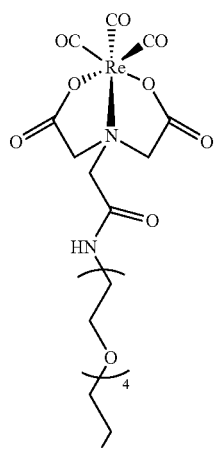

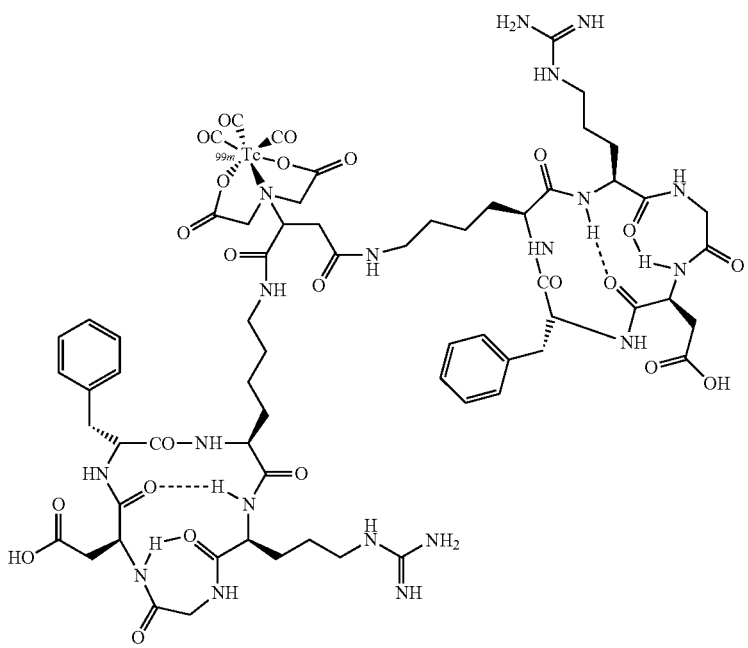

The target compound was prepared by the same method as the one applied in Example 13, except for using the precursor compound of Formula 2b at Example 2 instead of the precursor compound of formula 2a at Example 1.

For HPLC, the same condition as the one at Example 6 was applied, and the target compound of Example 14 was detected at 21.4 minute by a gamma-ray detector (NaI). Accordingly, a 0.2-minute difference was noticed from the retention time (21.6 minute) of detecting the target compound of Example 18 at the detector (UV 214 nm). The radiochemical yield was achieved 60-70% (decay corrected), with the radiochemical purity exceeding 97%.

Example 15

Preparation of (tricarbonyl-[$^{99m}$Tc]technetium-N-α-bis-hydroxycarbonyl methyl-aspartic acid)-[cyclic (lysine-alginine-glycine-aspartic acid-D-phenylalanine)]$_2$ The target compound was prepared by the same method as the one applied in Example 13, except for using the precursor compound of Formula 2c at Example 3 instead of the precursor compound of formula 2a at Example 1.

For HPLC, the same condition as the one at Example 6 was applied, and the target compound of Example 15 was detected at 18.4 minute by a gamma-ray detector (NaI). Accordingly, a 0.8 minute difference was noticed from the retention time (19.2 minute) of detecting the target compound of Example 8 at the detector (UV 214 nm). The radiochemical yield was achieved 60-70% (decay corrected), with the radiochemical purity exceeding 97%.

Example 16

Preparation of (tricarbonyl-[$^{99m}$Tc]technetium-N-α-bis-hydroxycarbonyl methyl-glycine-CONH(CH$_2$CH$_2$O)$_4$CH$_2$CH$_2$CONH-lysine)-[cyclic (lysine-alginine-glycine-aspartic acid-D-phenylalanine)]$_2$

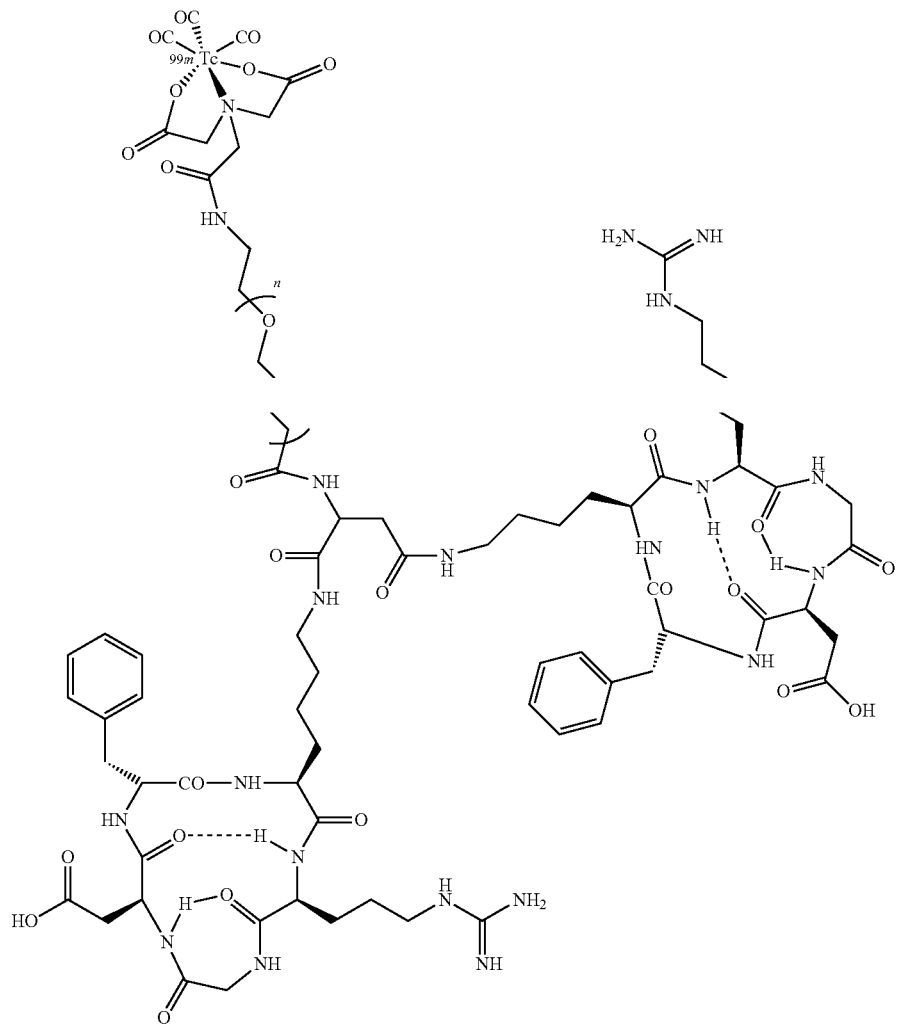

n = 4

The target compound was prepared by the same method as the one applied in Example 13, except for using the precursor compound of Formula 2e at Example 5 instead of the precursor compound of formula 2a at Example 1.

For HPLC, the same condition as the one at Example 6 was applied, and the target compound of Example 16 was detected at 19.9 minute by a gamma-ray detector (NaI). Accordingly, a 0.9 minute difference was noticed from the retention time (20.8 minute) of detecting the target compound of Example 9 at the detector (UV 214 nm). The radiochemical yield achieved 50-70% (decay corrected), with the radiochemical purity exceeding 97%.

In the compounds of Examples 13 to 16, the nonradioisotope $^{185/187}$Re of the compounds of Examples 6 to 8 are changed to radioisotope $^{99m}$Tc, according to which there was about 1-minute difference of the retention times (tR) in the HPLC as verified through the mass spectrometry between the respective compounds of Examples 6, 7, 8 and the compounds of Examples 13, 14, 16. Accordingly, because most precursors were labeled with high yield, it was confirmed that the compounds of Examples 13 to 16 had change of technetium-99m only (both technetium and rhenium belong to the same metallic ion family in the periodic table, and have the identical reactivity with the same precursor).

Experimental Example 1

Measurement of Biological Activity of Tricarbonyl Technetium-99m or Rhenium-188 Labeled Cyclic RGD Derivative <1-1> Measurement of Affinity ($IC_{50}$)

The following experiment was conducted to investigate binding affinity of tricarbonyl technetium or rhenium labeled cyclic RGD derivative according to the present invention to integrin $\alpha_v\beta_3$ the key angiogenesis biomarker.

Human Umbilical Vein Endothelial Cell (HUVEC) known to overexpress integrin $\alpha_v\beta_3$ was incubated in endothelial cell basal medium-2 (EBM-2) containing FBS, hydrocortisone, human fibroblast growth factor-basic (hFGF-B), vascular endothelial growth factor (VEGF), R3-IGF-1, ascorbic acid, human epidermal growth factor (hEGF), GA-1000, and heparin at 37° C. under 5% $CO_2$. $1 \times 10^6$ of HUVEC was seeded in eppendorf tube, 2 µCi of tricarbonyl technetium-99m or rhenium-188 labeled cyclic RGD derivative was added, and at the same time, 0, 0.01, 0.05, 0.1, 0.2, 0.3, 0.4, 0.5, 1, 3, 5 nM of cyclic RGD (cRGDyV) as a reference substance for competitive reaction were added to each tube, and then binding reaction was induced at 37° C., under 5% $CO_2$ for 1 hour. After the incubation, the HUVEC was washed three times with 100 mM PBS, and radioactivity of specifically-binding tricarbonyl technetium or rhenium labeled cyclic RGD derivative via the competition reaction was measured with a gamma counter. Nonlinear regression curve was constructed using the measured radiation energy and the values per concentration of the reference substances of the competitive reaction, and $IC_{50}$ was calculated based on the curve. For the calculation of the $IC_{50}$, sigma plot software was used.

The binding affinity ($IC_{50}$) to integrin $\alpha_v\beta_3$ was then measured as listed in the following table.

TABLE 1

| | $IC_{50}$ (nM) |
|---|---|
| Example 10 | 1.4 |
| Example 12 | 0.5 |
| Example 13 | 1.6 |
| Example 14 | 1.2 |
| Example 15 | 0.4 |
| Example 16 | 0.5 |

Referring to Table 1, the compounds of Examples 13 and 10, each being the derivative introduced with one cyclic RGD, exhibited $IC_{50}$ of 1.6 nM and 1.4 nM, respectively, and thus indicated the fact that the binding affinity to integrin $\alpha_v\beta_3$ did not vary when the same precursor was used with a change of radioisotope only. Example 14 also confirmed the fact that introduction of PEG linkers did not make great influence compared to Examples 13 and 10. The compounds of Examples 15 and 12, each being derivative introduced with two cyclic RGDs, exhibited 0.4 nM and 0.5 nM, the binding value of sub nanomol, respectively, thus indicating the excellent affinity. Likewise, the binding affinity to integrin $\alpha_v\beta_3$ did not vary regardless of whether or not technetium-99m and rhenium-188 are introduced to the same precursor, and that there was no noticeable influence on the binding affinity between Example 16 introduced with the PEG linkers and Examples 12 and 15.

Accordingly, it was confirmed that the cyclic RGD derivative according to the present invention exhibits higher binding affinity to integrin 003, as the number of introduced cyclic RGDs increases.

<1-2> Evaluation of Uptake and Excretion of Tricarbonyl Technetium-99m Labeled Cyclic RGD Derivative in/from Tumor and Normal Organ in In Vivo Tumor Model Mice The rates of uptake and excretion in tumor and normal organ were investigated via experiment on the three types of tricarbonyl technetium-99m labeled cyclic RGD derivatives (Examples 13-15) according to the present invention, using mice with congenital absence of the thyroid (7 week-old, BALB/c-nu Sic strain, hereinbelow, "nude mice").

To form a tumor in nude mice, human glioblastoma U87-MG cell ($1 \times 10^6/100$ µL in PBS) was subcutaneously injected, and the models that formed 0.4-0.5 cc sized tumor after approximately 2 weeks of growth period, were used in the experiment.

Figure 2:
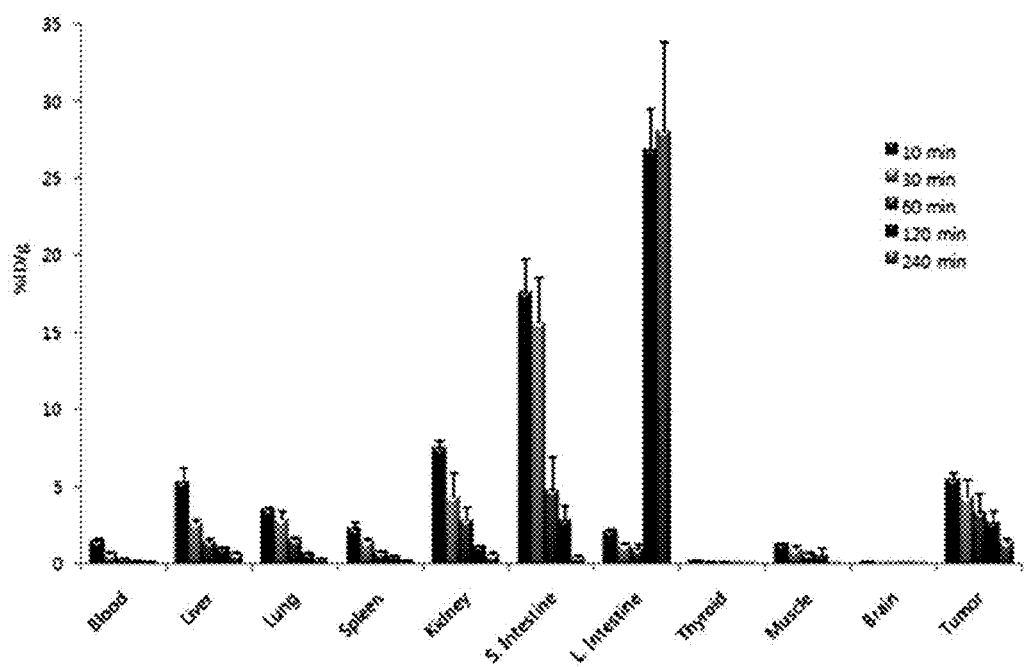
FIG. 2 is a graph showing the result of measuring uptake and excretion rates of tricarbonyl technetium-99m labeled cyclic RGD derivative according to another embodiment of the present invention in/from in vivo tumor model mice.
Figure 3:
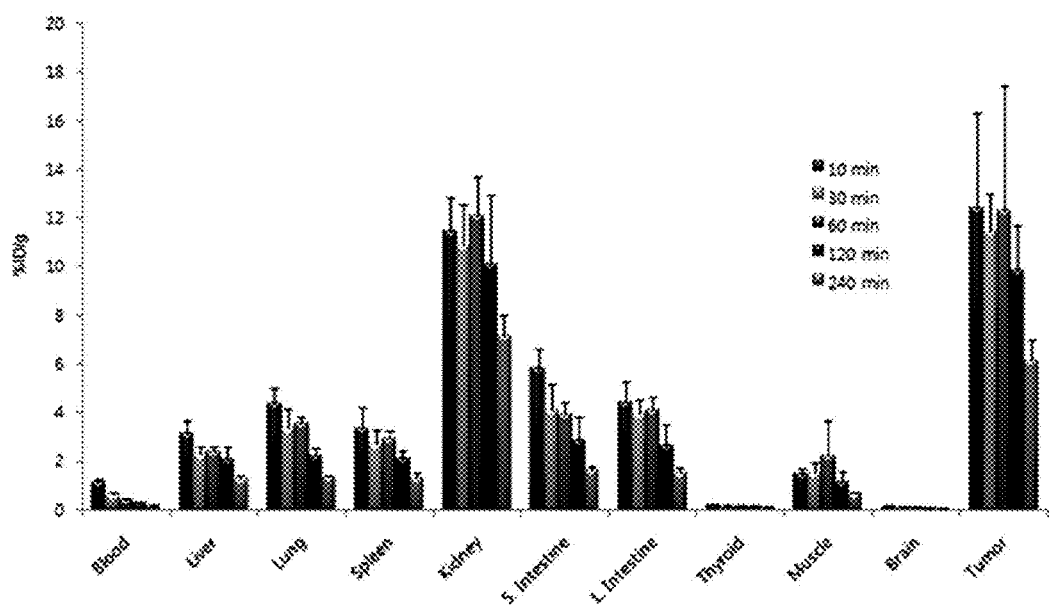
FIG. 3 is a graph showing the result of measuring uptake and excretion rates of tricarbonyl technetium-99m labeled cyclic RGD derivative according to yet another embodiment of the present invention in/from in vivo tumor model mice.

The compounds prepared at Examples 13-15 were dissolved in saline, and injected to tail vein of each model by 100 µL (20 µCi). Time course of in vivo distribution was set to 10, 30, 60, 120, 240 minutes, and 4-5 models were used per each time. The mice were sacrificed at each time and blood, tumor and the respective organs (including liver, lung, spleen, kidneys, small intestine, large intestine, thyroid, muscle, brain) were taken, and the weight (g) of the respective organs and radioactivity of the drug was measured with a gamma counter. The radioactivity of the respective organs was calculated in the unit of % ID/g (percent injected dose per gram) as shown in FIGS. 1-3. % ID/g was calculated by:

$$\% \text{ ID/g} = (\text{drug intake/injected amount of drug} \times 100) / \text{weight of each organ (g)} \quad \text{[Mathematical formula 1]}$$

The measurements are listed in Tables 2-4 provided below.

TABLE 2

| Compound of Example 13 | | | | |
|---|---|---|---|---|
| organ | 10 min | 30 min | 60 min | 120 min |
| Blood | 0.37 ± 0.04 | 0.10 ± 0.01 | 0.03 ± 0.00 | 0.02 ± 0.00 |
| Liver | 5.12 ± 0.76 | 0.92 ± 0.10 | 0.45 ± 0.09 | 0.30 ± 0.09 |
| Lung | 1.72 ± 0.86 | 0.54 ± 0.14 | 0.27 ± 0.07 | 0.40 ± 0.46 |
| Spleen | 0.56 ± 0.32 | 0.19 ± 0.10 | 0.152 ± 0.03 | 0.08 ± 0.03 |
| Kidneys | 1.65 ± 0.48 | 0.50 ± 0.09 | 0.23 ± 0.02 | 0.13 ± 0.01 |
| Small intestine | 4.41 ± 1.00 | 5.59 ± 0.86 | 3.95 ± 0.22 | 4.00 ± 0.41 |
| Large intestine | 0.55 ± 0.37 | 0.31 ± 0.06 | 0.53 ± 0.81 | 0.11 ± 0.01 |
| Thyroid | 0.05 ± 0.02 | 0.01 ± 0.00 | 0.01 ± 0.00 | 0.03 ± 0.03 |
| Muscle | 0.56 ± 0.27 | 0.16 ± 0.04 | 0.08 ± 0.07 | 0.05 ± 0.02 |
| Brain | 0.04 ± 0.01 | 0.02 ± 0.00 | 0.01 ± 0.01 | 0.03 ± 0.02 |
| Tumor | 1.43 ± 0.15 | 0.78 ± 0.40 | 0.10 ± 0.14 | 0.33 ± 0.06 |

TABLE 3

| Compound of Example 14 | | | | | |
|---|---|---|---|---|---|
| organ | 10 min | 30 min | 60 min | 120 min | 240 min |
| Blood | 1.43 ± 0.23 | 0.66 ± 0.09 | 0.35 ± 0.06 | 0.17 ± 0.02 | 0.11 ± 0.01 |
| Liver | 5.30 ± 0.95 | 2.62 ± 0.28 | 1.41 ± 0.21 | 0.98 ± 0.15 | 0.64 ± 0.08 |
| Lung | 3.50 ± 0.18 | 2.87 ± 0.56 | 1.52 ± 0.19 | 0.65 ± 0.08 | 0.32 ± 0.02 |

TABLE 3-continued

| | Compound of Example 14 | | | | |
|---|---|---|---|---|---|
| organ | 10 min | 30 min | 60 min | 120 min | 240 min |
| Spleen | 2.31 ± 0.36 | 1.45 ± 0.18 | 0.77 ± 0.07 | 0.47 ± 0.10 | 0.20 ± 0.02 |
| Kidneys | 7.54 ± 0.46 | 4.33 ± 1.60 | 2.80 ± 0.89 | 1.13 ± 0.11 | 0.61 ± 0.14 |
| Small intestine | 17.60 ± 2.20 | 15.56 ± 2.89 | 4.97 ± 2.13 | 2.77 ± 0.96 | 0.37 ± 0.17 |
| Large intestine | 2.06 ± 0.25 | 1.21 ± 0.20 | 0.98 ± 0.30 | 26.78 ± 2.80 | 28.06 ± 5.82 |
| Thyroid | 0.20 ± 0.04 | 0.12 ± 0.03 | 0.08 ± 0.02 | 0.03 ± 0.00 | 0.01 ± 0.00 |
| Muscle | 1.31 ± 0.02 | 0.97 ± 0.19 | 0.66 ± 0.13 | 0.52 ± 0.47 | 0.07 ± 0.01 |
| Brain | 0.10 ± 0.01 | 0.07 ± 0.01 | 0.06 ± 0.01 | 0.04 ± 0.02 | 0.02 ± 0.00 |
| Tumor | 5.43 ± 0.50 | 4.27 ± 1.15 | 3.35 ± 1.23 | 2.63 ± 0.74 | 1.41 ± 0.24 |

TABLE 4

| | Compound of Example 15 | | | | |
|---|---|---|---|---|---|
| organ | 10 min | 30 min | 60 min | 120 min | 240 min |
| Blood | 1.16 ± 008 | 0.62 ± 0.11 | 0.42 ± 0.01 | 0.26 ± 0.05 | 0.16 ± 0.02 |
| Liver | 3.10 ± 0.58 | 2.24 ± 0.33 | 2.36 ± 0.21 | 2.06 ± 0.54 | 1.24 ± 0.19 |
| Lung | 4.34 ± 0.69 | 3.34 ± 0.80 | 3.55 ± 0.26 | 2.19 ± 0.35 | 1.33 ± 0.09 |
| Spleen | 3.33 ± 0.89 | 2.67 ± 0.63 | 2.92 ± 0.29 | 2.12 ± 0.32 | 1.29 ± 0.21 |
| Kidneys | 11.47 ± 1.36 | 10.85 ± 1.71 | 12.09 ± 1.62 | 10.12 ± 2.82 | 7.14 ± 0.85 |
| Small intestine | 5.82 ± 0.80 | 4.10 ± 1.09 | 3.90 ± 0.48 | 2.85 ± 0.99 | 1.62 ± 0.18 |
| Large intestine | 4.42 ± 0.85 | 3.93 ± 0.57 | 4.08 ± 0.53 | 2.63 ± 0.84 | 1.54 ± 0.20 |
| Thyroid | 0.19 ± 0.03 | 0.15 ± 0.02 | 0.14 ± 0.03 | 0.12 ± 0.04 | 0.10 ± 0.02 |
| Muscle | 1.48 ± 0.21 | 1.49 ± 0.44 | 2.23 ± 1.44 | 1.11 ± 0.43 | 0.64 ± 0.07 |
| Brain | 0.13 ± 0.02 | 0.10 ± 0.02 | 0.10 ± 0.01 | 0.08 ± 0.01 | 0.06 ± 0.01 |
| Tumor | 12.44 ± 3.89 | 11.45 ± 1.53 | 12.31 ± 5.15 | 9.81 ± 1.92 | 6.15 ± 0.84 |

Referring to Tables 2 to 4 and FIGS. 1 to 3, the time course of uptake and excretion of the compounds of Examples 13 to 15 in/from tumor and organs indicated the following: The compound of Example 13 had low uptake in tumor and high intake in liver and small intestine in an initial time, and excreted fast from the entire organs over time. 10 minutes post-injection, the liver uptake that exceeded 5% ID/g was fast excreted over time to become as low as 0.3% ID/g after 2 hours. After metabolization in the liver, most drug was confirmed to have been excreted outside the body, and from the fact that the level of 4% ID/g was maintained even after 2 hours of the injection, it was confirmed that the active intestine excretion was going on. Any specific uptake was not found in the other organs such as brain and muscle including blood, and based on the fact that the uptake in the thyroid was maintained at a range of 0.01-0.05% ID/g, the stability of the drug in vivo was confirmed. The initial uptake in tumor was fast, which changed from 1.43% ID/g at 10 minutes after injection to 0.33% ID/g at 2 hours after injection, and then gradually decreased after then.

The compound of Example 14 was prepared by linking PEG chain to lysine of the cyclic RGD to reduce offset effect between the negative charge (−) of the label pocket and the positive charge (+) of the alginine of the cyclic RGD. The time course of uptake and excretion of the compound of Example in tumor and organs were as follows: the uptake was 5.3% ID/g at 10 minutes post-injection, and the drug was fast metabolized over time to become as low as 0.64% ID/g at 4 hours post-injection. It was also observed that the drug metabolized in liver was excreted out of the body mostly through the intestines. From the finding that the drug absorption in large intestine rapidly increased as the drug passed the small intestine at 2 hours post-injection, it was confirmed that the drug begins to excrete out of the body at such time. A small amount of drug was collected in the bladder via filtration at the kidneys, which was then excreted out of the body with the urine. No specific absorption was found in the brain and muscles including blood, and the uptake in the thyroid was also maintained in a range of 0.01-0.20% ID/g, thereby indicating the stability of the drug in vivo. The uptake in tumor was relatively high, which was 5.43% ID/g at 10 minutes post-injection, and according to the progress of metabolism, the uptake slowly decreased to become 1.41% ID/g at 4 hours post-injection.

The compound introduced with two cyclic RGDs showed very low initial absorption in the liver which was 3.1% ID/g at 10 minutes post-injection and very fast liver metabolism which resulted in rapid decline to 1% ID/g at 4 hours. After metabolization in the liver, the drug was rapidly passed through the kidneys and excreted out of the body in urine, and the maximum uptake in the kidneys was at 1 hour post-injection, exceeded 12% ID/g 60 minutes after the injection due to excretion via urine. The excretion of drug via intestines including small and large intestines was as low as 5% ID/g, and it was confirmed that most administered drug was excreted via urine. Specific uptake in brain and muscles including blood was not shown, and from the fact that the uptake in the thyroid was continuously maintained at 0.1% ID/g, the drug stability was confirmed. The initial uptake in drug for the first 10 minutes was as high as 12.44% ID/g, which displayed high and fast ability to accumulate in tumor and the uptake was maintained up to 1 hour after the injection. After that, slow release of the drug from the tumor was observed, but still, the uptake in tumor was high enough to exceed 6% ID/g 4 hours after the injection.

<1-3> Evaluation by SPECT Imaging of Tricarbonyl Technetium-99m Cyclic RGD Derivative on In Vivo Tumor Model Mice The tumor model mice were prepared by the same method as the one applied at Experimental Example <1-2>. The compounds (0.5-1 mCi) of Examples 13-15 according to the present invention were dissolved in 100 μL saline and injected to tail veins of the tumor-bearing mouse models. The animal models were anesthetized by 2% isofluorane gas for the image acquisition time, and static images of the mice were acquired for 180 minutes from the injection with SPECT apparatus (Bioscan, nanoSPECT/CT). The imaging protocol consisted of repetition of emission and transmission as follows:

[20 min emission+transmission]×9 times

Figure 4:
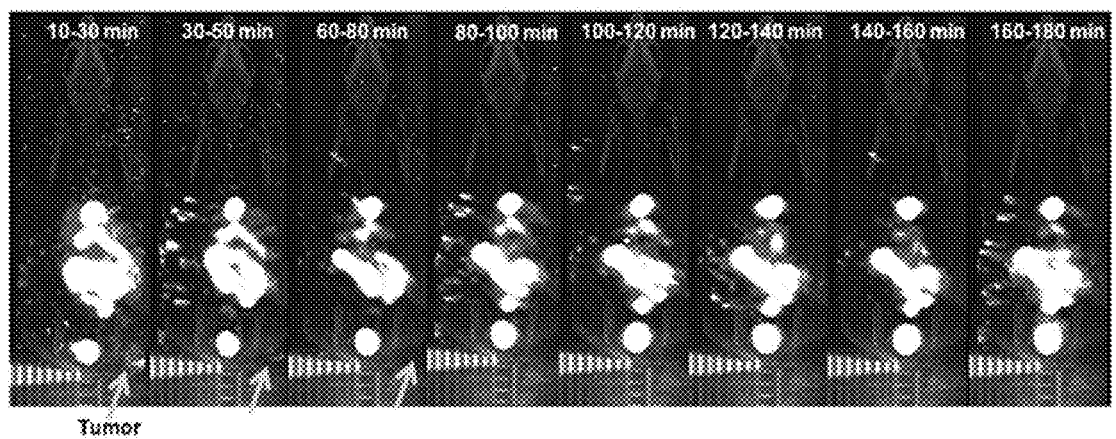
FIG. 4 are SPECT images of tricarbonyl technetium-99m labeled cyclic RGD derivative according to an embodiment of the present invention in in vivo tumor model mouse.
Figure 5:
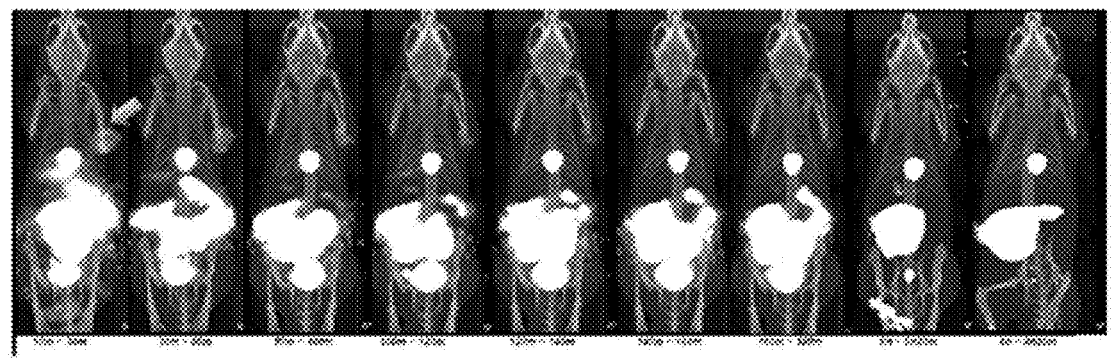
FIG. 5 are SPECT images of tricarbonyl technetium-99m labeled cyclic RGD derivative according to another embodiment of the present invention in in vivo tumor model mice.
Figure 6:
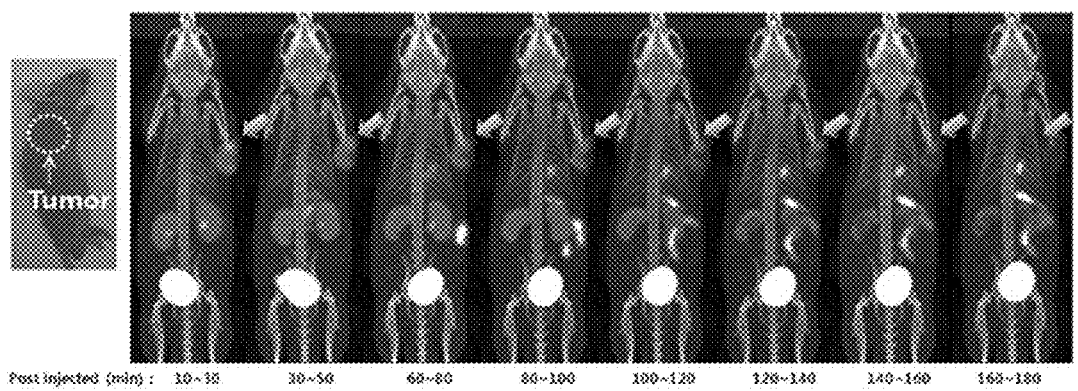
FIG. 6 are SPECT images of tricarbonyl technetium-99m labeled cyclic RGD derivative according to yet another embodiment of the present invention in in vivo tumor model mouse.

The SPECT images of the compounds of Examples 13-15 are shown in FIGS. 4 to 6.

The compound of Example 13 was absorbed in tumor after minutes from the injection, and this was continuously observed for about 1 hour. Most drugs passed the metabolization in the liver and then ware fast discharged to the intestines, while only some drug was excreted in the urine via the kidneys.

The compound of Example 14 exhibited high absorption rate in tumor after 10 minutes from the injection, and this was observed for about three hours. Similarly to the compound of Example 13, it was observed that the compound of Example 14 was fast discharged to the intestines after liver metabolization, while only some drug was excreted in the urine via the kidneys.

Figure 7:
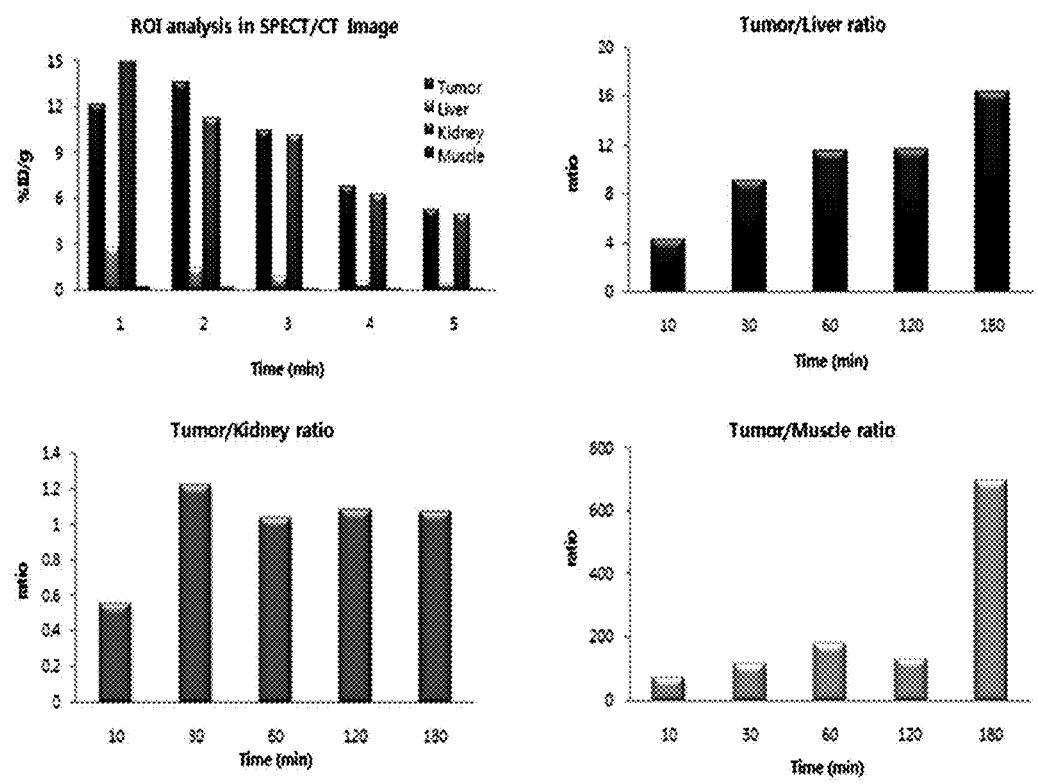
FIG. 7 are graphs showing the level of organ-uptake in a time-dependent manner and ratios of uptake of tricarbonyl technetium-99m labeled cyclic RGD derivative according to an embodiment of the present invention in in vivo tumor model mice, and tumor-to-liver, tumor-to-kidneys and tumor-to-normal cell uptake rates in each time.

The compound of Example 15 shows very high absorption rate in tumor after the first 10 minutes from the injection, and this was continuously observed for three hours and longer. Differently from the compounds of Examples 13 and 14, most metabolized drug was excreted in the urine via the kidneys. FIG. 7 shows graphical representation of the relative uptake rates in liver, kidneys and muscles with reference to tumor, according to which the rates of uptake and excretion in/from tumor and respective organs of the compound of Example 15 (Table 4) can be evaluated, and identity in the SPECT imaging evaluation of the compound of Example 15 (FIG. 6) can be observed.

<1-4> SPECT Imaging Evaluation of Tricarbonyl Technetium-99m Cyclic RGD Derivative after Injection with Cyclic RGD Derivative (cRGDyV), the Competition Reaction Reference Substance, in In Vivo Tumor Model Mice In order to investigate the tumor-specific uptake of cyclic RGD derivative, cyclic RGD (cRGDyV) as competitive reaction reference substance was administered and SPECT/CT imaging was acquired. For the reference substance, cyclic RGD-tyrosine-valine derivative was injected to tail vein in a concentration of 18 mg/Kg. After 10 minutes from the injection of the reference substance, the compound of Example 15 (1 mCi/200 μL) labeled with technetium-99m was injected to tail vein. Upon injection, SPECT/CT images were acquired under following conditions:

The animal models were anesthetized with 2% isofluorane gas for the duration of image acquisition time, and the tumor size of the animal models was 0.4 cc. CT images were taken under condition of 45 v, 178 μA for 4 min and 30 sec., and acquired at 10 minute intervals for total 9 times (i.e., for 90 minutes after the injection). The results are shown in FIG. 8.

Figure 8:
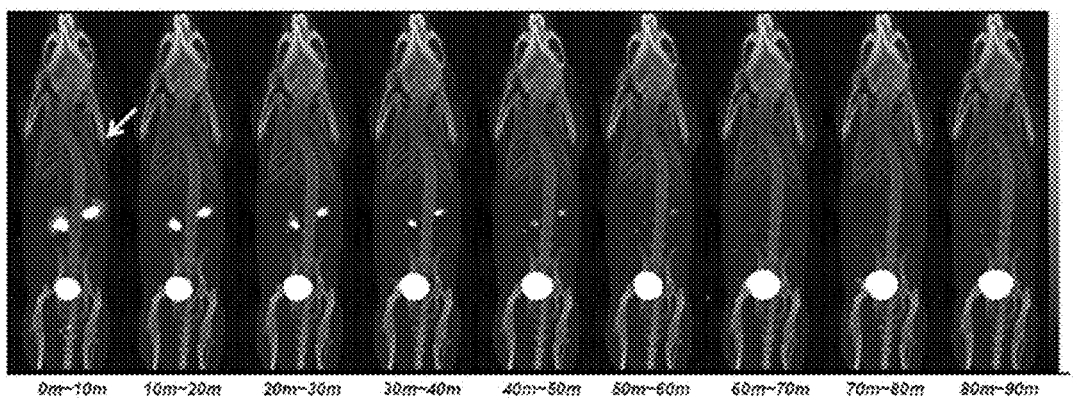
FIG. 8 are SPECT images of tricarbonyl technetium-99m labeled cyclic RGD derivative according to an embodiment of the present invention in in vivo tumor model mice after the mice were administered with cyclic RGD derivative (cRGDyV, 18 mg/kg)

Referring to FIG. 8, after administration of cyclic RGD (cRGDyV), known for specific binding to integrin $\alpha_v\beta_3$, the SPECT images of the compound of Example 15 according to the present invention revealed that the absorption in tumor was reduced 94% or more at 25 minutes post-injection, compared to the images of the compound of Example 15 of FIG. 6. That is the tumor images due to $\alpha_v\beta_3$ integrin-specific binding were confirmed.

<1-5> Evaluation of Tumor Growth Suppression and Treatment Performances of Tricarbonyl Rhenium-188 Labeled Cyclic RGD Derivative in In Vivo Tumor Model Mice (I)

Treatment effect experiment was conducted to investigate the ability of tricarbonyl rhenium-188 labeled cyclic RGD derivative to suppress tumor growth.

The rhenium-188 labeled cyclic RGD derivative of Example 5 was injected once in a week, for four weeks. The models to determine treatment effect were divided into small radioactive injection group (300 μCi) and large radioactive injection group (600 μCi), and at the same time, a control group injected with sterilized saline and a comparative group injected with 100 μg of cyclic RGD (cRGDyV) intraperitoneally everyday, were also set. The compound of Example 11 and the sterilized saline were administered through tail veins. The CT images was taken once a week, to visually measure the growth and size of the subcutaneous tumor. The tumor was actually measured three times a week using Vernier Calipers, and the weights of the animal models were also consistently measured three times a week for total 4 weeks. The result was constructed into a graphic representation which is shown in FIG. 9.

Figure 9:
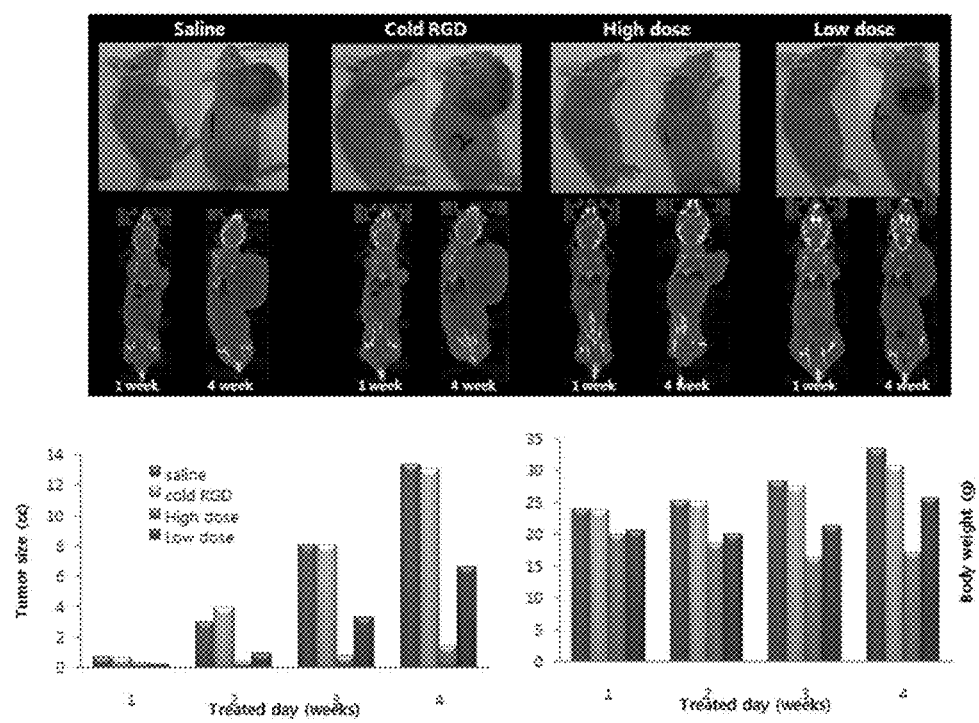
FIG. 9 are showing influence of the tricarbonyl rhenium-188 labeled cyclic RGD derivative according to an embodiment of the present invention on the tumor size and weight of the model mice.

Referring to FIG. 9, the groups administered with sterilized saline and cyclic RGD showed rapid growth of tumor over time from the initial tumor size of 0.69 cc, 0.7 cc. At 2 week, the tumor grew to 3.0 cc and 3.9 cc, respectively, and both groups showed 8.0 cc of tumor size at 3 week. At last week of treatment, the tumors were 13.0 cc and 12.9 cc, which were very fast growth pattern. The rate of tumor growth in the two groups had no meaningful difference from each other, and the weights also greatly increased from the initial measurement of 23 g to 33 g for the group administered with sterilized saline and 30 g for the group administered with cyclic RGD. This is considered to be attributed to rapid growth of tumor in the animal models. The initial tumor size of the group administered with 300 μCi of the compound of Example 11 was 0.23 cc and this increased to 0.66 cc when the treatment for four weeks was ended. Compared to the groups administered with sterilized saline or cyclic RGD, approximately 50% of tumor growth suppression ability was confirmed. The weight change due to radiation energy showed increase from 20 g before treatment to 25 g after the 4-week-long treatment, but considering the fact that the weight of the animals was actually decreased during the treatment, the weight increase of about 5 g is considered to be attributed to the tumor which was grown. The tumor growth in the group administered with 600 μCi with more emission of radiation energy showed very slow rate of growth which changed from 0.3 cc at initial measurement, to 0.3 cc at week 2, 0.7 cc at 3 week and 1.4 cc at the end of the treatment, which therefore confirmed approximately 90% of tumor growth suppression ability compared to the group administered with sterilized saline and the group administered with cyclic RGD, and approximately 79% of tumor growth suppression ability compared to the group administered with low radiation energy treatment (300 μCi). The weight change of the animals due to high dose of radiation energy from the four times of administration of the drug gradually decreased from 19.9 g before treatment to 17.09 g at the end of the treatment by approximately 14%. Therefore, the result is in agreement with the regulation of the Institutional Review Boards (IRB) that weight decrease of the test subject should not exceed 20% before and after the radiotherapy of the tumor.

<1-6> Tumor Growth Suppression and Treatment Performance of Tricarbonyl Rhenium-188 Labeled Cyclic RGD Derivative in In Vivo Tumor Model Mice (II)

The two in vivo tumor model mice with the same tumor size (0.3 cc) were divided into a model injected with the compound (600 µCi/200 µL) of Example 12, i.e., rhenium-188 labeled cyclic RGD derivative, and the other model without being injected with the compound of Example 12. The SPECT imaging result on the two models using the compound of Example 15 after three days is shown in FIG. 10.

The small-animal SPECT/CT was used to acquire static imaging of the mice for 60 minutes after the injection. The imaging protocol consisted of repetition of emission and transmission as follows:

[10 min emission+transmission]×6 times

Figure 10:
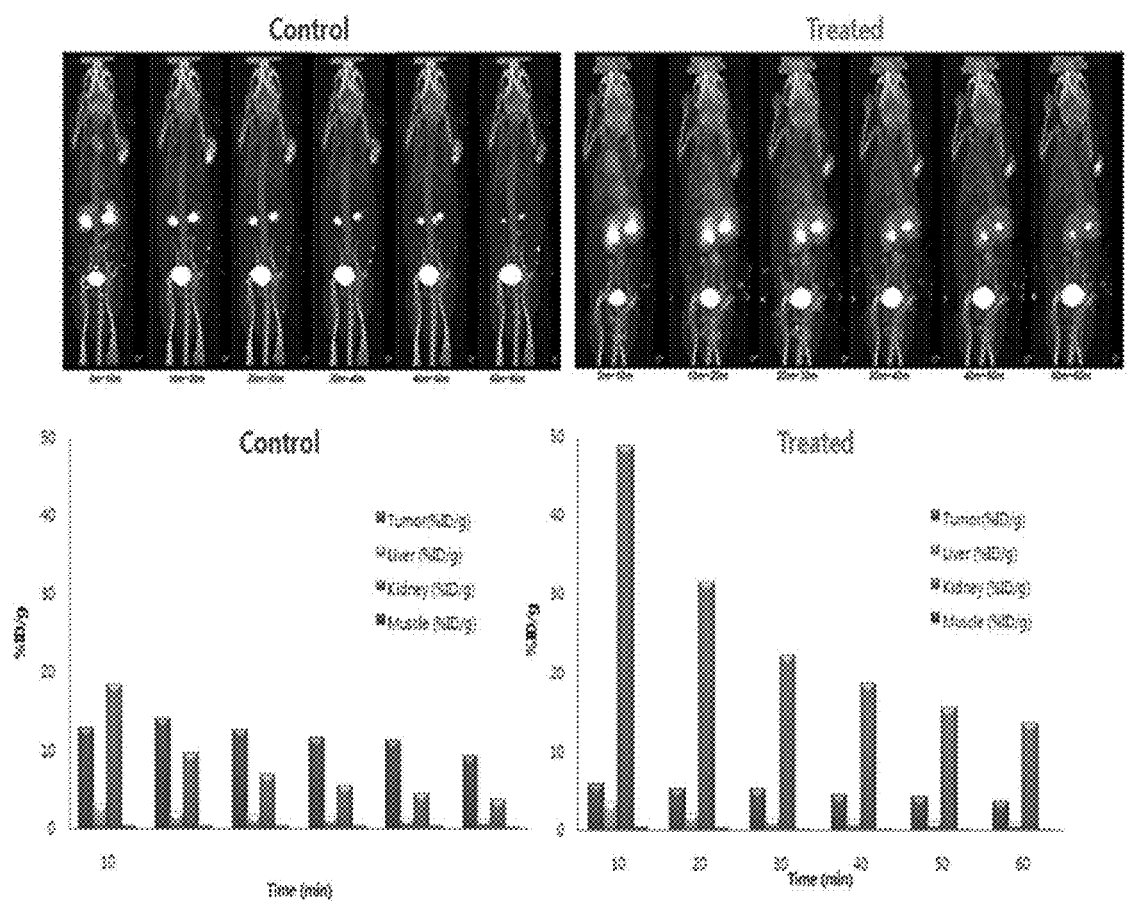
FIG. 10 are SPECT images and graphs of uptake rates in interested organ area, suggesting the influence of tricarbonyl rhenium-188 labeled cyclic RGD derivative according to an embodiment of the present invention on the tumor size and weight of the model mice.
Figure 11:
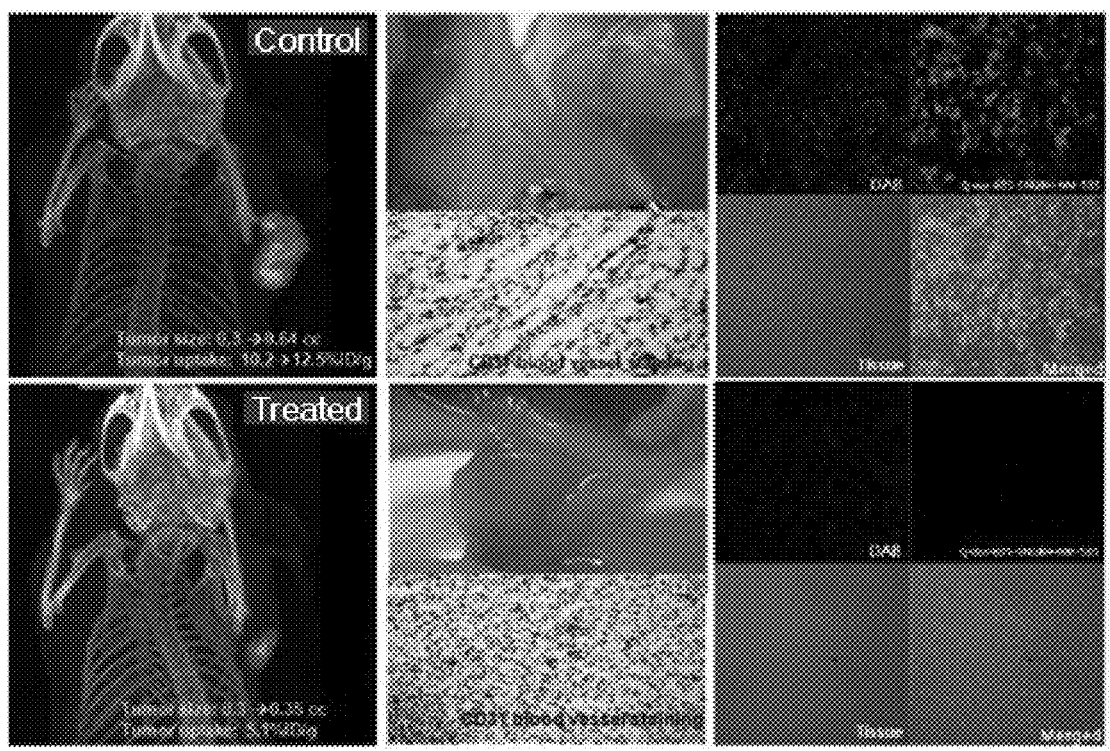
FIG. 11 are confocal microscopic images using CD-31 blood staining and Q-dot-dimeric RGD derivative, obtained after administration of tricarbonyl technetium-99m labeled cyclic RGD derivative according to an embodiment of the present invention, showing the influence of the tricarbonyl technetium-99m labeled cyclic RGD derivative on the tumor size and uptake rate in tumor.

The relative uptake rates in tumor, liver, kidneys and muscles between the group administered with the compound of Example 12 and the normal group were analyzed on a graphical representation as shown in FIG. 10, and after direct removal of the tumors from the two groups, the distribution of blood vessels around the tumor were photographed as shown in FIG. 11.

Referring to FIGS. 10 and 11, the model injected with the compound of Example 6 grew from the initial size of 0.3 cc to 0.35 cc, while the non-administered model showed 0.65 cc of tumor size. For the purpose of SPECT imaging comparison of the tumor, the group administered with the compound of Example 15 (i.e., technetium-99m labeled cyclic RGD derivative) was compared, and it was confirmed that the uptake rate in tumor reduced by 59% in the group administered with the compound of Example 12. Further, unlike the non-administered model, the tumor photographs taken from the two groups exhibited that the model administered with the compound of Example 12 had noticeably less distribution of ambient blood vessels and also the rapid reduction of blood vessels surrounding the tumor. Further, by CD31 blood vessel staining the tumor tissue slice, no clear vessels were observed in the tumor cells administered with the compound of Example 12. Further, in the experiment of evaluating integrin $\alpha_v\beta_3$ distribution using two RGD derivatives introduced with Q-dot in the tumor tissue slice, most integrin was damaged in the tumor tissues administered with the compound of Example 12 (FIG. 11).

Accordingly, tricarbonyl rhenium-188 labeled cyclic RGD derivative according to the present invention provides excellent suppression on the growth and angiogenesis of tumor, and can be advantageously used in the treatment of a diseases derived from the angiogenesis of the tumor.

Meanwhile, the compound according to the present invention may be provided in various dosage forms. A few examples of the dosage forms that may contain the compound according to the present invention as an active ingredient will be provided below for the illustrative purpose, but the present embodiment will not be strictly limited to any specific example only.

Preparative Example

Preparation of Injection

| Compound of Formula 1 of the present invention | 5 mCi |
|---|---|
| Ethanol | 100 mg |
| Saline | 2000 mg |

The compound of Formula 1 according to the present invention was dissolved with ethanol or not in distilled water, passed through sterilized filter, stored in sterilized vial, and prepared into an injection according to known methods.

The foregoing embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

What is claimed is:

1. Tricarbonyl technetium-99m, rhenium-188, or rhenium-185/187 labeled cyclic RGD derivative selected from the group consisting of compounds expressed by Chemical Formula 1A, 1B, and 1C or a pharmaceutically acceptable salt thereof:

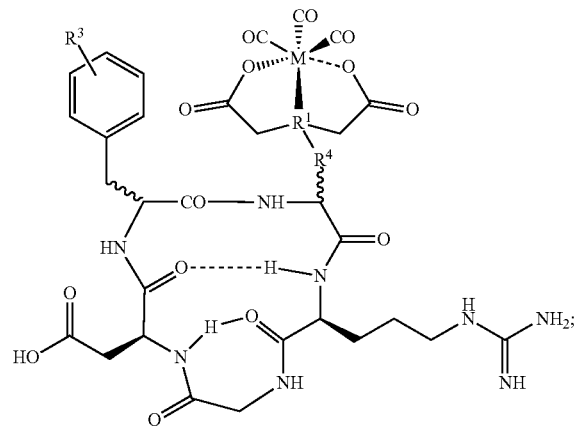

Chemical Formula 1A wherein,

M is $^{99m}$Tc, $^{188}$Re, or $^{185/187}$Re;

$R^1$ is N, $N(CH_2CH_2O)_nCH_2CH_2CONH$ or $N(CH_2CONH)(CH_2CH_2O)_4CH_2CH_2CONH$;

n is an integer between 0 and 8;

$R^3$ is H or OH;

$R^4$ is $-(CH_2)_m-$ or $-(CH_2)_m-COO-$; and m is an integer between 1 and 8,

Chemical Formula 1B

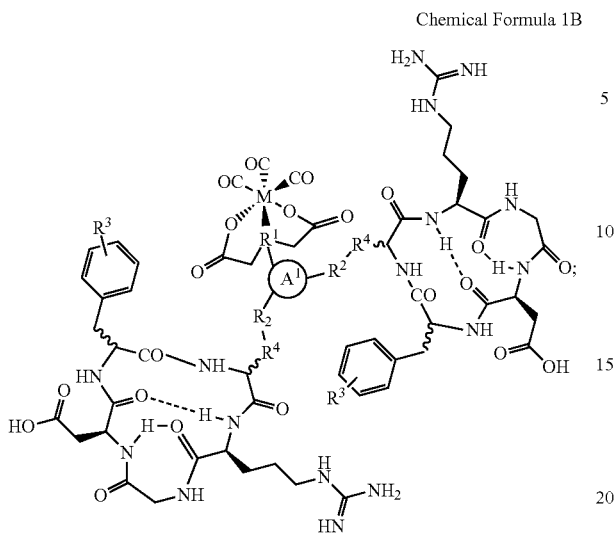

wherein,
M is $^{99m}$Tc, $^{188}$Re, or $^{185/187}$Re;
R$^1$ is N, N(CH$_2$CH$_2$O)$_n$CH$_2$CH$_2$CONH or N(CH$_2$CONH)(CH$_2$CH$_2$O)$_4$CH$_2$CH$_2$CONH;
A$^1$ is an amino acid selected from the group consisting of aspartic acid, lysine, glutamic acid, tyrosine, cysteine, threonine, and serine;
R$^2$ is NH or NH(Z)$_n$CH$_2$CH$_2$CONH;
Z is —CH$_2$CH$_2$O— or —CH$_2$CONH—;
n is an integer between 0 and 8;
R$^3$ is H or OH;
R$^4$ is —(CH$_2$)$_m$— or —(CH$_2$)$_m$—COO—; and
m is an integer between 1 and 8,
and wherein,
M is $^{99m}$Tc, $^{188}$Re, or $^{185/187}$Re;
R$^1$ is N, N(CH$_2$CH$_2$O)$_n$CH$_2$CH$_2$CONH or N(CH$_2$CONH)(CH$_2$CH$_2$O)$_4$CH$_2$CH$_2$CONH;
A$^1$ and A$^2$ are each an amino acid selected from the group consisting of aspartic acid, lysine, glutamic acid, tyrosine, cysteine, threonine, and serine;
R$^2$ is NH or NH(Z)$_n$CH$_2$CH$_2$CONH;
Z is —CH$_2$CH$_2$O— or —CH$_2$CONH—;
n is an integer between 0 and 8;
R$^3$ is H or OH;
R$^4$ is —(CH$_2$)$_m$— or —(CH$_2$)$_m$—COO—; and
m is an integer between 1 and 8.

2. The tricarbonyl technetium-99m, rhenium-188, or rhenium 185/187 labeled cyclic RGD derivative as set forth in claim 1, wherein the tricarbonyl technetium-99m, rhenium-188, or rhenium-185/187 labeled cyclic RGD derivative is selected from the group consisting of:

cyclic {(tricarbonyl-[$^{99m}$Tc]technetium-N-α-bis-hydroxycarbonyl methyl-lysine)-alginine-glycine-aspartic acid-D-phenylalanine};

cyclic {(tricarbonyl-[$^{188}$Re]rhenium-N-α-bis-hydroxycarbonyl methyl-lysine)-alginine-glycine-aspartic acid-D-phenylalanine};

cyclic {(tricarbonyl-[$^{185/187}$Re]rhenium-N-α-bis-hydroxycarbonyl methyl-lysine)-alginine-glycine-aspartic acid-D-phenylalanine};

cyclic {(tricarbonyl-[$^{99m}$Tc]technetium-N-α-bis-hydroxycarbonyl methyl-NH$_2$(CH$_2$CH$_2$O)$_4$CH$_2$CH$_2$CONH-lysine)-alginine-glycine-aspartic acid-D-phenylalanine};

Chemical Formula 1C

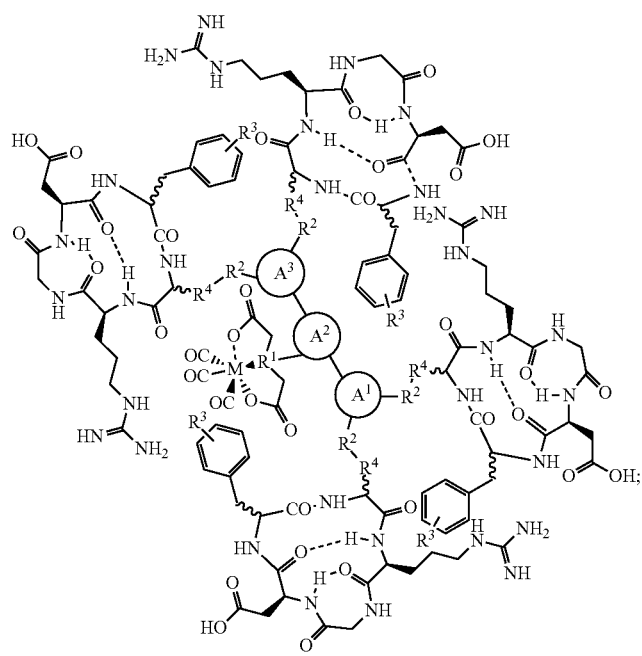

cyclic {(tricarbonyl-[$^{188}$Re]rhenium-N-α-bis-hydroxycarbonyl methyl-NH$_2$(CH$_2$CH$_2$O)$_4$CH$_2$CH$_2$CONH-lysine)-alginine-glycine-aspartic acid-D-phenylalanine};

cyclic {(tricarbonyl-[$^{185/187}$Re]rhenium-N-α-bis-hydroxycarbonyl methyl-NH$_2$(CH$_2$CH$_2$O)$_4$CH$_2$CH$_2$CONH-lysine)-alginine-glycine-aspartic acid-D-phenylalanine};

cyclic {(tricarbonyl-[$^{99m}$Tc]technetium-N-α-bis-hydroxycarbonyl methyl-glycine-CONH(CH$_2$CH$_2$O)$_4$CH$_2$CH$_2$CONH-lysine)-alginine-glycine-aspartic acid-D-phenylalanine};

cyclic {(tricarbonyl-[$^{188}$Re]rhenium-N-α-bis-hydroxycarbonyl methyl-glycine-CONH(CH$_2$CH$_2$O)$_4$CH$_2$CH$_2$CONH-lysine)-alginine-glycine-aspartic acid-D-phenylalanine};

cyclic {(tricarbonyl-[$^{185/187}$Re]rhenium-N-α-bis-hydroxycarbonyl methyl-glycine-CONH(CH2CH$_2$O)$_4$CH$_2$CH$_2$CONH-lysine)-alginine-glycine-aspartic acid-D-phenylalanine};

(tricarbonyl-[$^{99m}$Tc]technetium-N-α-bis-hydroxycarbonyl methyl-aspartic acid)-[cyclic (lysine-alginine-glycine-aspartic acid-D-phenylalanine)]$_2$;

(tricarbonyl-[$^{188}$Re]rhenium-N-α-bis-hydroxycarbonyl methyl-aspartic acid)-[cyclic (lysine-alginine-glycine-aspartic acid-D-phenylalanine)]$_2$;

(tricarbonyl-[$^{185/187}$Re]rhenium-N-α-bis-hydroxycarbonyl methyl-aspartic acid)-[cyclic (lysine-alginine-glycine-aspartic acid-D-phenylalanine)]$_2$;

{tricarbonyl-[$^{99m}$Tc]technetium-N-α-bis-hydroxycarbonyl methyl-(polyethylene glycol)$_n$-aspartic acid}-[cyclic (lysine-alginine-glycine-aspartic acid-D-phenylalanine)]$_2$, (n=0-8);

{tricarbonyl-[$^{188}$Re]rhenium-N-α-bis-hydroxycarbonyl methyl-(polyethylene glycol)$_n$-aspartic acid}-[cyclic (lysine-alginine-glycine-aspartic acid-D-phenylalanine)]$_2$, (n=0-8);

{tricarbonyl-[$^{185/187}$Re]rhenium-N-α-bis-hydroxycarbonyl methyl-(polyethylene glycol)$_n$-aspartic acid}-[cyclic (lysine-alginine-glycine-aspartic acid-D-phenylalanine)]$_2$, (n=0-8);

{tricarbonyl-[$^{99m}$Tc]technetium-N-α-bis-hydroxycarbonyl methyl-(polyethylene glycol)$_n$-aspartic acid}-{(polyethylene glycol)$_n$-[cyclic (lysine-alginine-glycine-aspartic acid-D-phenylalanine)]}$_2$, (n=0-8);

{tricarbonyl-[$^{188}$Re]rhenium-N-α-bis-hydroxycarbonyl methyl-(polyethylene glycol)$_n$-aspartic acid}-{(polyethylene glycol)$_n$-[cyclic (lysine-alginine-glycine-aspartic acid-D-phenylalanine)]}$_2$, (n=0-8);

{tricarbonyl-[$^{185/187}$Re]rhenium-N-α-bis-hydroxycarbonyl methyl-(polyethylene glycol)$_n$-aspartic acid}-{(polyethylene glycol)$_n$-[cyclic (lysine-alginine-glycine-aspartic acid-D-phenylalanine)]}$_2$, (n=0-8);

(tricarbonyl-[$^{99m}$Tc]technetium-N-α-bis-hydroxycarbonyl methyl-aspartic acid)-{aspartic acid-[cyclic (lysine-alginine-glycine-aspartic acid-D-phenylalanine)]$_2$}$_4$;

(tricarbonyl-[$^{188}$Re]rhenium-N-α-bis-hydroxycarbonyl methyl-aspartic acid)-{aspartic acid-[cyclic (lysine-alginine-glycine-aspartic acid-D-phenylalanine)]$_2$}$_4$;

(tricarbonyl-[$^{185/187}$Re]rhenium-N-α-bis-hydroxycarbonyl methyl-aspartic acid)-{aspartic acid-[cyclic (lysine-alginine-glycine-aspartic acid-D-phenylalanine)]$_2$}$_4$;

{tricarbonyl-[$^{99m}$Tc]technetium-N-α-bis-hydroxycarbonyl methyl-(polyethylene glycol)$_n$-aspartic acid}-{aspartic acid-[cyclic (lysine-alginine-glycine-aspartic acid-D-phenylalanine)]$_2$}$_4$, (n=0-8);

{tricarbonyl-[$^{188}$Re]rhenium-N-α-bis-hydroxycarbonyl methyl-(polyethylene glycol)$_n$-aspartic acid}-{aspartic acid-[cyclic (lysine-alginine-glycine-aspartic acid-D-phenylalanine)]$_2$}$_4$, (n=0-8);

{tricarbonyl-[$^{185/187}$Re]rhenium-N-α-bis-hydroxycarbonyl methyl-(polyethylene glycol)$_n$-aspartic acid}-{aspartic acid-[cyclic (lysine-alginine-glycine-aspartic acid-D-phenylalanine)]$_2$}$_4$, (n=0-8);

{tricarbonyl-[$^{99m}$Tc]technetium-N-α-bis-hydroxycarbonyl methyl-(polyethylene glycol)$_n$-aspartic acid}-{aspartic acid-(polyethylene glycol)$_n$-[cyclic (lysine-alginine-glycine-aspartic acid-D-phenylalanine)]$_2$}$_4$, (n=0-8);

{tricarbonyl-[$^{188}$Re]rhenium-N-α-bis-hydroxycarbonyl methyl-(polyethylene glycol)$_n$-aspartic acid}-{aspartic acid-(polyethylene glycol)$_n$-[cyclic (lysine-alginine-glycine-aspartic acid-D-phenylalanine)]$_2$}$_4$, (n=0-8); and {tricarbonyl-[$^{185/187}$Re]rhenium-N-α-bis-hydroxycarbonyl methyl-(polyethylene glycol)$_n$-aspartic acid}-{aspartic acid-(polyethylene glycol)$_n$-[cyclic (lysine-alginine-glycine-aspartic acid-D-phenylalanine)]$_2$}$_4$, (n=0-8).

3. A preparation method of the tricarbonyl technetium-99m or tricarbonyl rhenium-188 labeled cyclic RGD derivative selected from a group of compounds expressed by Chemical Formula 1A, 1B, and 1C comprising:

reacting tricarbonyl technetium-99m ($^{99m}$Tc(CO)$_3$(H$_2$O)$_3^+$) or tricarbonyl rhenium-188 ($^{188}$Re(CO)$_3$(H$_2$O)$_3^+$) with a precursor compound of Chemical Formula 2A, 2B, or 2C to prepare the tricarbonyl technetium-99m or rhenium-188 labeled cyclic RGD derivative of Chemical Formula 1A, 1B, or 1C, respectively:

Chemical Formula 1A

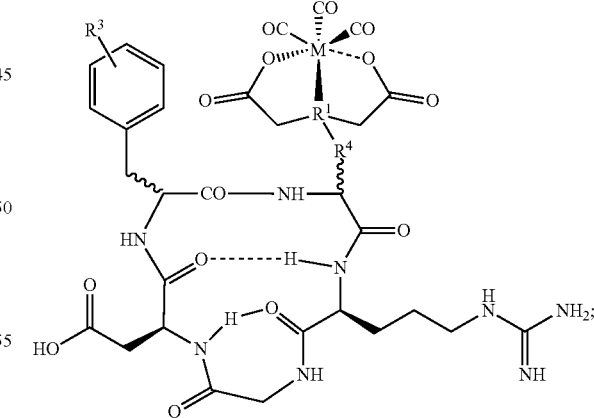

wherein,

M is $^{99m}$Tc or $^{188}$Re;

R$^1$ is N, N(CH$_2$CH$_2$O)$_n$CH$_2$CH$_2$CONH or N(CH$_2$CONH)(CH$_2$CH$_2$O)$_4$CH$_2$CH$_2$CONH;

n is an integer between 0 and 8;

R$^3$ is H or OH;

R$^4$ is —(CH$_2$)$_m$— or —(CH$_2$)$_m$—COO—; and m is an integer between 1 and 8,

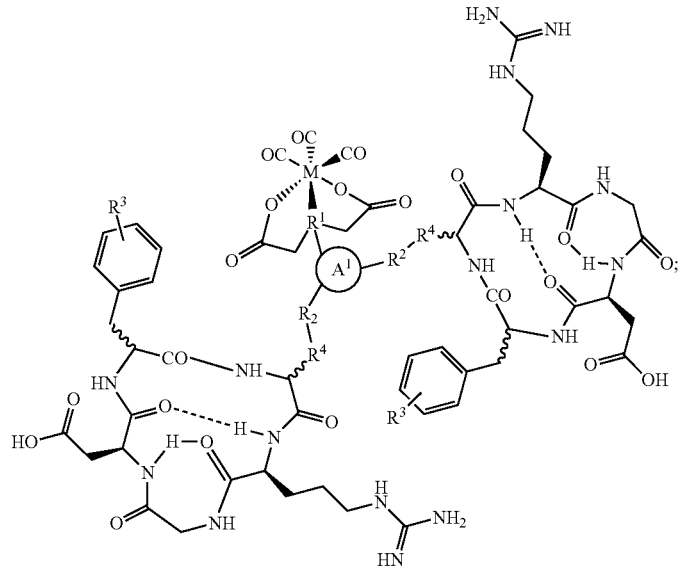

Chemical Formula 1B wherein,
M is $^{99m}$Tc or $^{188}$Re;
R$^1$ is N, N(CH$_2$CH$_2$O)$_n$CH$_2$CH$_2$CONH or N(CH$_2$CONH)(CH$_2$CH$_2$O)$_4$CH$_2$CH$_2$CONH;
A$^1$ is an amino acid selected from the group consisting of aspartic acid, lysine, glutamic acid, tyrosine, cysteine, threonine, and serine;
R$^2$ is NH or NH(Z)$_n$CH$_2$CH$_2$CONH;
Z is —CH$_2$CH$_2$O— or —CH$_2$CONH—;
n is an integer between 0 and 8;
R$^3$ is H or OH;
R$^4$ is —(CH$_2$)$_m$— or —(CH$_2$)$_m$—COO—; and
m is an integer between 1 and 8,
and

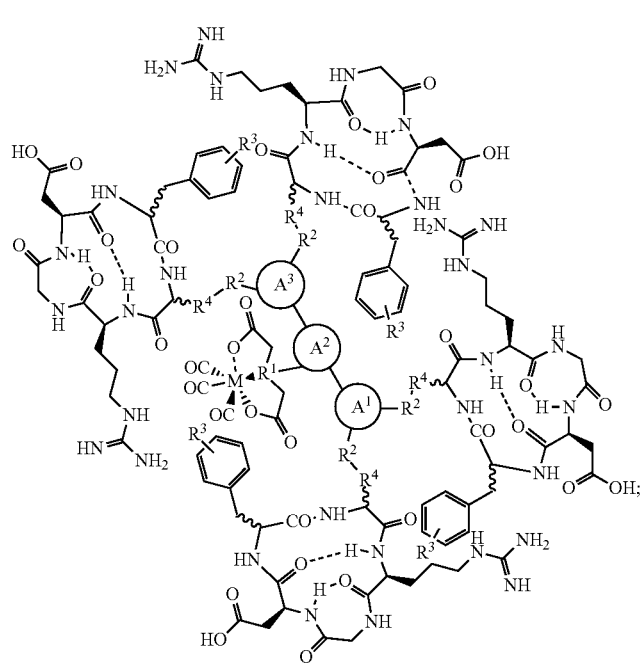

Chemical Formula 1C wherein,

M is $^{99m}$Tc or $^{188}$Re;

$R^1$ is N, $N(CH_2CH_2O)_nCH_2CH_2CONH$ or $N(CH_2CONH)(CH_2CH_2O)_4CH_2CH_2CONH$;

$A^1$ and $A^2$ are each an amino acid selected from the group consisting of aspartic acid, lysine, glutamic acid, tyrosine, cysteine, threonine, and serine;

$R^2$ is NH or $NH(Z)_nCH_2CH_2CONH$;

Z is $-CH_2CH_2O-$ or $-CH_2CONH-$;

n is an integer between 0 and 8;

$R^3$ is H or OH;

$R^4$ is $-(CH_2)_m-$ or $-(CH_2)_m-COO-$; and m is an integer between 1 and 8,

Chemical Formula 2A

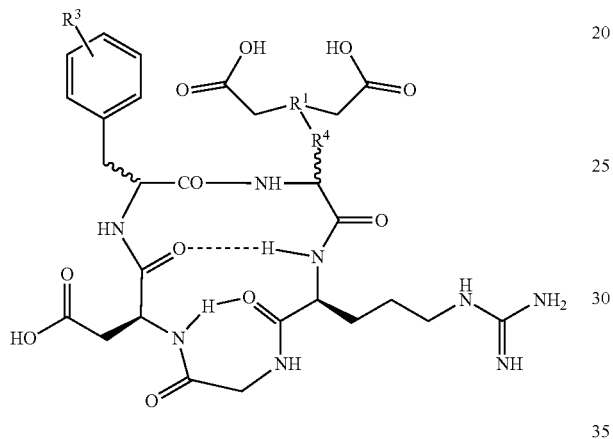

wherein $R^1$, $R^3$, and $R^4$ are as defined in Chemical Formula 1A,

Chemical Formula 2B

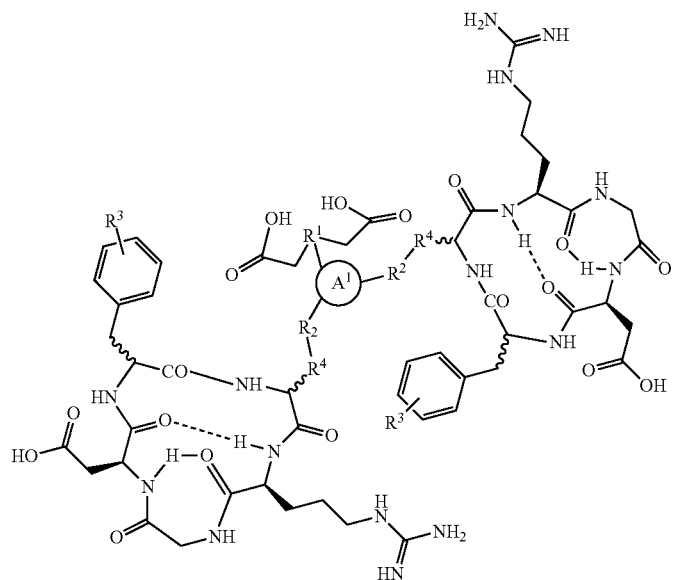

wherein $R^1$, $R^2$, $R^3$, $R^4$, and $A^1$ are as defined in Chemical Formula 1B, Chemical Formula 2C

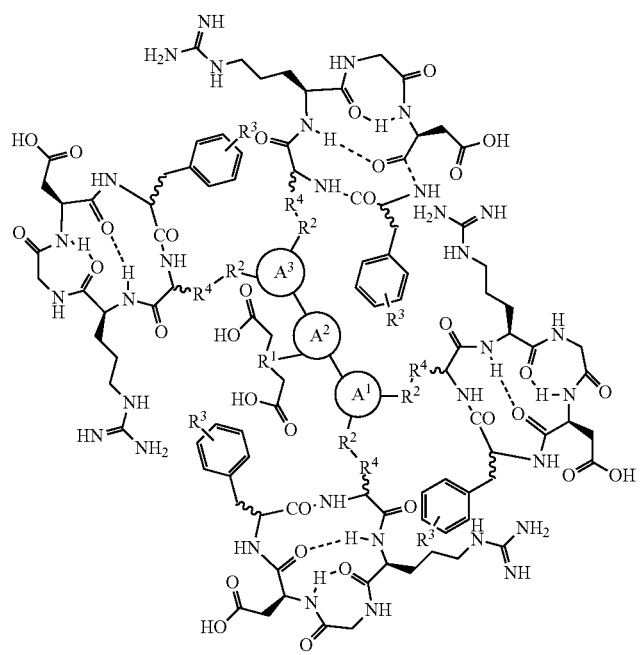

wherein R¹, R², R³, R⁴, A¹, and A² are as defined in Chemical Formula 1C.

4. The preparation method as set forth in claim 3 comprising:

diluting the tricarbonyl technetium-99m or tricarbonyl rhenium-188 in 0.5-5 mL of distilled water, adding the solution of the tricarbonyl technetium-99m or tricarbonyl rhenium-188 in water to the precursor of Chemical Formula 2A, 2B, or 2C in a reaction container, and heating the mixture of the tricarbonyl technetium-99m or tricarbonyl rhenium-188 and the precursor at 70-80° C. for 30 or 60 minutes, to thereby prepare the tricarbonyl technetium-99m or tricarbonyl rhenium-188 labeled cyclic RGD derivative of Chemical Formula 1A, 1B, or 1C, respectively.

5. A preparation method of the tricarbonyl rhenium-185/187 labeled cyclic RGD derivative comprising:

introducing $(NEt_4)_2{}^{185/187}Re(CO)_3Br_3$ into a precursor compound of Chemical Formula 2A, 2B, or 2C to react, thereby preparing cyclic RGD derivative of Chemical Formula 1A, 1B, or 1C, respectively:

Chemical Formula 1A

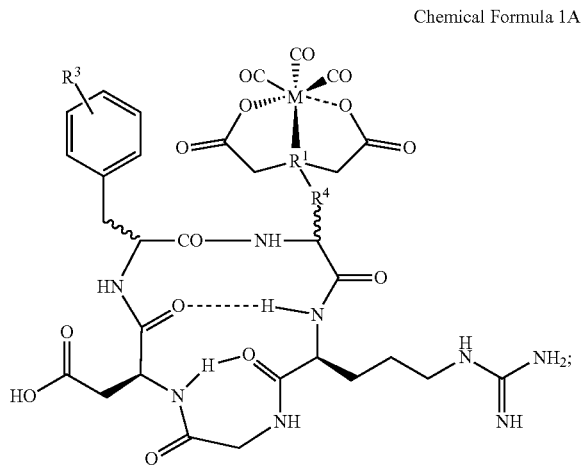

wherein,

M is $^{185/187}Re$;

R¹ is N, $N(CH_2CH_2O)_nCH_2CH_2CONH$ or $N(CH_2CONH)(CH_2CH_2O)_4CH_2CH_2CONH$;

n is an integer between 0 and 8;

R³ is H or OH;

R⁴ is $-(CH_2)_m-$ or $-(CH_2)_m-COO-$; and m is an integer between 1 and 8,

Chemical Formula 1B

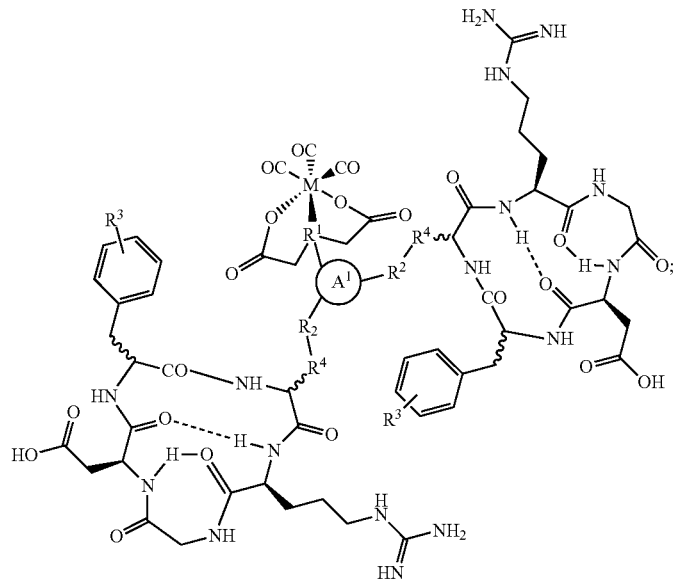

wherein,
M is $^{185/187}$Re;
$R^1$ is N, N(CH$_2$CH$_2$O)$_n$CH$_2$CH$_2$CONH or N(CH$_2$CONH)(CH$_2$CH$_2$O)$_4$CH$_2$CH$_2$CONH;
$A^1$ is an amino acid selected from the group consisting of aspartic acid, lysine, glutamic acid, tyrosine, cysteine, threonine, and serine;
$R^2$ is NH or NH(Z)$_n$CH$_2$CH$_2$CONH;
Z is —CH$_2$CH$_2$O— or —CH$_2$CONH—;
n is an integer between 0 and 8;
$R^3$ is H or OH;
$R^4$ is —(CH$_2$)$_m$— or —(CH$_2$)$_m$—COO—; and
m is an integer between 1 and 8,
and Chemical Formula 1C

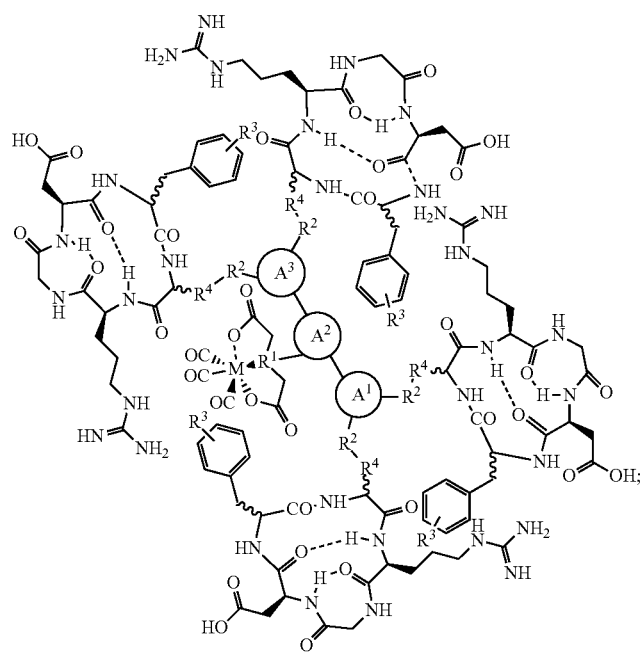

wherein,

M is $^{185/187}$Re;

$R^1$ is N, $N(CH_2CH_2O)_nCH_2CH_2CONH$ or $N(CH_2CONH)(CH_2CH_2O)_4CH_2CH_2CONH$;

$A^1$ and $A^2$ are each an amino acid selected from the group consisting of aspartic acid, lysine, glutamic acid, tyrosine, cysteine, threonine, and serine;

$R^2$ is NH or $NH(Z)_nCH_2CH_2CONH$;

Z is —$CH_2CH_2O$— or —$CH_2CONH$—;

n is an integer between 0 and 8;

$R^3$ is H or OH;

$R^4$ is —$(CH_2)_m$— or —$(CH_2)_m$—COO—; and m is an integer between 1 and 8,

Chemical Formula 2A

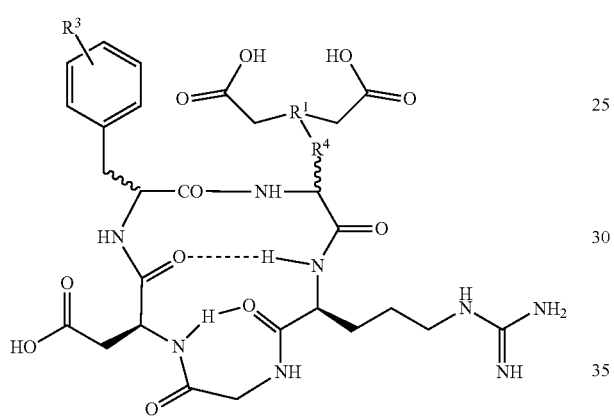

wherein $R^1$, $R^3$, and $R^4$ are as defined in Chemical Formula 1A,

Chemical Formula 2B

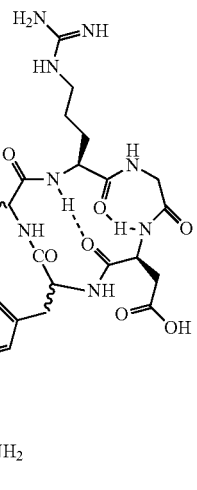

wherein $R^1$, $R^2$, $R^3$, $R^4$, and $A^1$ are as defined in Chemical Formula 1B, Chemical Formula 2C

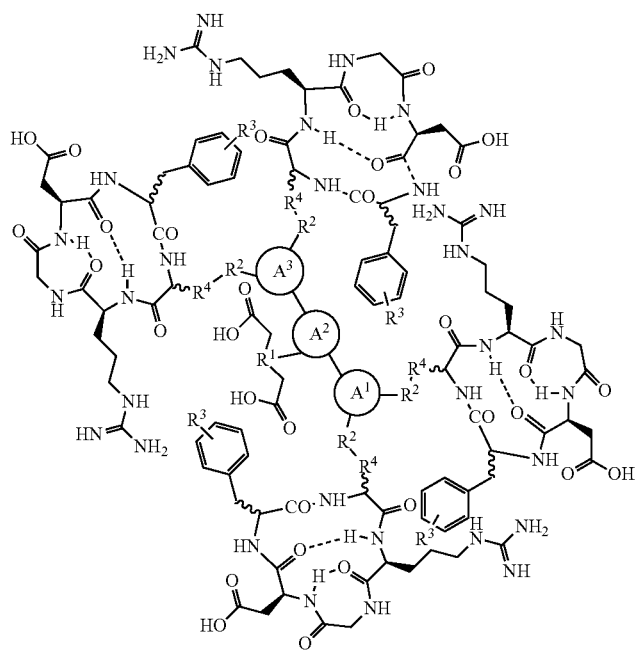

wherein $R^1$, $R^2$, $R^3$, $R^4$, $A^1$, and $A^2$ are as defined in Chemical Formula 1C.

6. The preparation method of claim 5 comprising:

diluting a reagent, $(NEt_4)_2{}^{185/187}Re(CO)_3Br_3$ in 0.5~5 mL of distilled water, adding the reagent solution to the precursor of Chemical Formula 2A, 2B, or 2C in a reaction container, and heating the mixture of the reagent and the precursor at 70-80° C. for 55-65 minutes, thereby preparing cyclic RGD derivative Chemical Formula 1A, 1B, or 1C, respectively.

7. A pharmaceutical composition comprising the tricarbonyl technetium-99m labeled cyclic RGD derivative or the pharmaceutically acceptable salt thereof as set forth in claim 1 as an active ingredient, and a pharmaceutically acceptable carrier.

8. A pharmaceutical composition comprising the tricarbonyl rhenium-188, or rhenium-185/187 labeled cyclic RGD derivative or the pharmaceutically acceptable salt thereof as set forth in claim 1 as an active ingredient, and a pharmaceutically acceptable carrier.

9. A method for diagnosing angiogenesis-related disease in a subject, comprising a step of administering a diagnostically effective amount of the tricarbonyl technetium-99m labeled cyclic RGD derivative and imaging the subject or the pharmaceutically acceptable salt, thereof as set forth in claim 1, wherein the angiogenesis-related disease is a disease with over-expression of integrin $\alpha_v\beta_3$ which is selected from the group consisting of thrombosis, myocardial ischemia, solid tumor, and metastatic tumor.

10. The method as set forth in claim 9, wherein the tricarbonyl technetium-99m labeled cyclic RGD derivative or the pharmaceutically acceptable salt thereof is administered by intravenous injection and the angiogenesis-related disease is diagnosed with single photon emission computer tomography (SPECT).

* * * * *